United States Patent [19]
Kónya et al.

[11] Patent Number: 6,123,723
[45] Date of Patent: Sep. 26, 2000

[54] DELIVERY SYSTEM AND METHOD FOR DEPOLYMENT AND ENDOVASCULAR ASSEMBLY OF MULTI-STAGE STENT GRAFT

[75] Inventors: András Kónya; Kenneth C. Wright; Sidney Wallace, all of Houston, Tex.

[73] Assignee: Board of Regents, The University of Texas System, Austin, Tex.

[21] Appl. No.: 09/259,105

[22] Filed: Feb. 26, 1999

Related U.S. Application Data

[60] Provisional application No. 60/076,383, Feb. 26, 1998.

[51] Int. Cl.$^7$ ......................................... A61F 2/06
[52] U.S. Cl. ........................................ 623/1.11; 606/108
[58] Field of Search ................................... 606/108, 191, 606/194, 198; 623/1, 12, 1.11

[56] References Cited

U.S. PATENT DOCUMENTS

| | | |
|---|---|---|
| D. 359,802 | 6/1995 | Fontaine . |
| 4,655,771 | 4/1987 | Wallsten . |
| 4,733,665 | 3/1988 | Palmaz . |
| 4,739,762 | 4/1988 | Palmaz . |
| 4,776,337 | 10/1988 | Palmaz . |
| 5,102,417 | 4/1992 | Palmaz . |
| 5,104,404 | 4/1992 | Wolff . |
| 5,135,536 | 8/1992 | Hillstead . |
| 5,219,355 | 6/1993 | Parodi et al. . |
| 5,282,824 | 2/1994 | Gianturco ................................ 606/198 |
| 5,360,443 | 11/1994 | Barone et al. . |
| 5,562,726 | 10/1996 | Chuter ......................................... 623/1 |
| 5,591,195 | 1/1997 | Taheri et al. . |
| 5,632,771 | 5/1997 | Boatman et al. . |
| 5,653,727 | 8/1997 | Wiktor ....................................... 623/1 |
| 5,669,936 | 9/1997 | Lazarus . |
| 5,709,701 | 1/1998 | Parodi ....................................... 623/1 |
| 5,713,917 | 2/1998 | Leonhardt et al. . |
| 5,716,396 | 2/1998 | Williams, Jr. . |
| 5,733,325 | 3/1998 | Robinson et al. ......................... 623/1 |
| 5,772,668 | 6/1998 | Summers et al. . |
| 5,830,229 | 11/1998 | Kónya et al. . |
| 5,851,228 | 12/1998 | Pinheiro ..................................... 623/1 |
| 5,860,998 | 1/1999 | Robinson et al. ....................... 606/194 |
| 5,876,432 | 3/1999 | Lau et al. . |
| 5,902,332 | 5/1999 | Schatz . |
| 5,913,896 | 6/1999 | Boyle et al. . |
| B1 4,655,771 | 9/1996 | Wallsten . |
| B1 4,733,665 | 1/1994 | Palmaz . |
| B1 4,739,762 | 10/1998 | Palmaz . |

FOREIGN PATENT DOCUMENTS

0701800A1  3/1996  European Pat. Off. .

OTHER PUBLICATIONS

Balko et al, "Transfemoral placement of intraluminal polyurethane prosthesis for abdominal aortic aneurysm," *J. Surg. Res.*, 40:305–309, 1986.

"Conformance by Design," World Medical Manufacturing Corporation.

World Medical News, 5(5), Feb. 1997.

Fallone et al, "Elastic characteristics of the self-expanding metallic stents," *Invest. Radiol.*, 23:370–376, 1988.

Zarins et al, "AneuRx stent graft versus open surgical repair of abdominal aortic aneurysms: multicenter prospective clinical trial," *J. Vasc. Surg.*, 29:292–308, 1999.

Letter to Sidney Wallace, dated Apr. 22, 1997, with two attachments.

Document entitled "Patient: #1115", faxed to András Kónya on Apr. 11, 1998.

(List continued on next page.)

*Primary Examiner*—Gene Mancene
*Assistant Examiner*—Eduardo C. Robert
*Attorney, Agent, or Firm*—Fulbright & Jaworski L.L.P.

[57] ABSTRACT

A multi-stage graft for implantation into a blood vessel is disclosed. The multi-stage stent graft may be used to repair aortic aneurysms. Each stage or layer may comprise radially compressible spring portions. The inner stages may be provided with or without a fabric covering. Also disclosed is a coaxial delivery system for the delivery and endovascular assembly of the multi-stage stent graft.

69 Claims, 19 Drawing Sheets

OTHER PUBLICATIONS

Kónya et al., "Endovascularly Assembled Aortic Graft: A Feasibility Study," JVIR Supplement, 8(1) Part 2, pp. 251–252, Jan.–Feb. 1997.

World Medical News, 5(6), May 1997.

Pictures of poster presented at SCVIR $22^{nd}$ Annual Scientific Meeting, Mar. 8–13, 1997, Sheraton Washington Hotel.

Descriptions on poster presented at SCVIR $22^{nd}$ Annual Scientific Meeting, Mar. 8–13, 1997, Sheraton Washington Hotel.

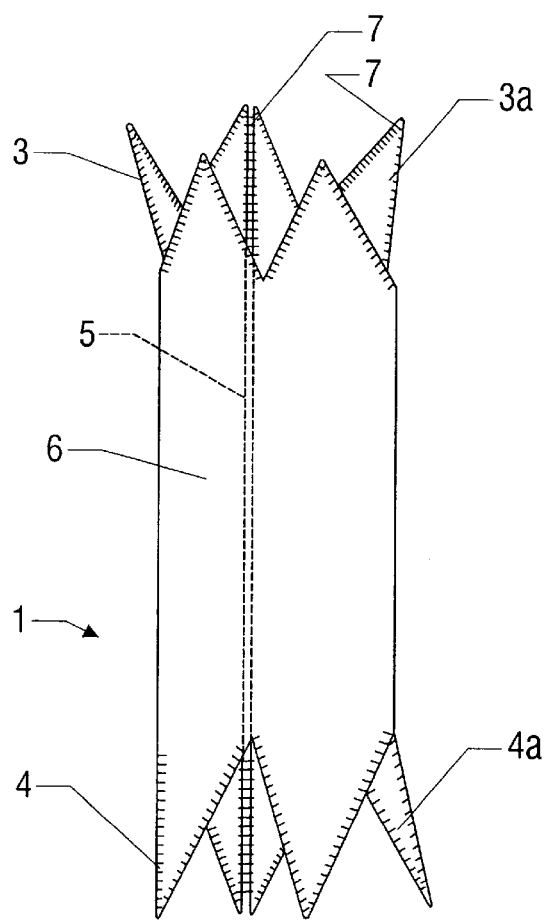
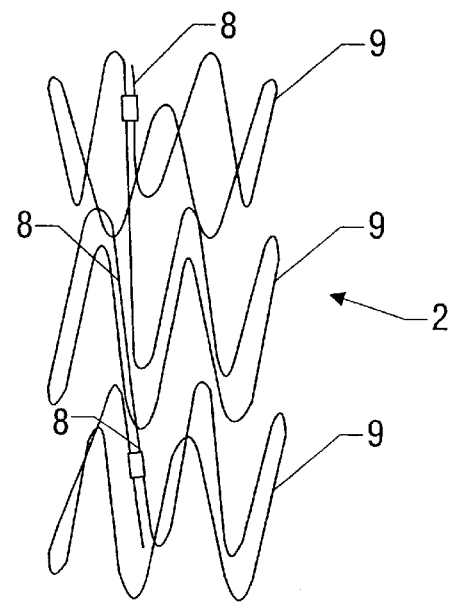
FIG. 1A
FIG. 1B

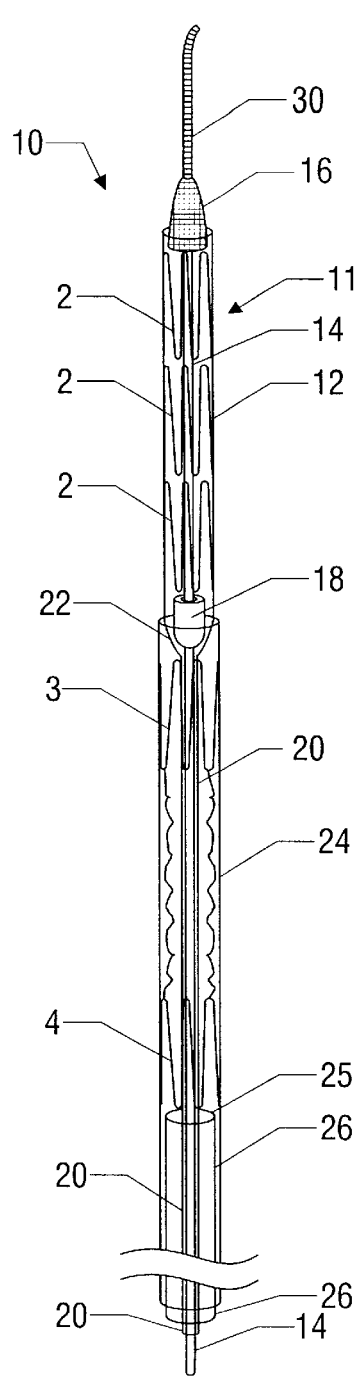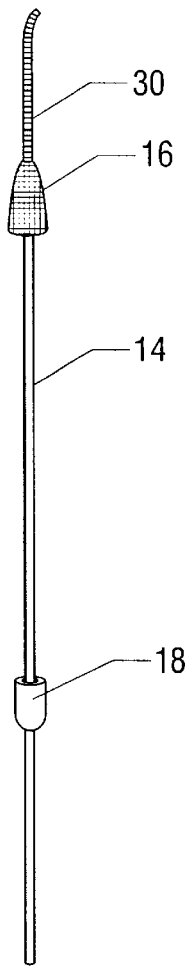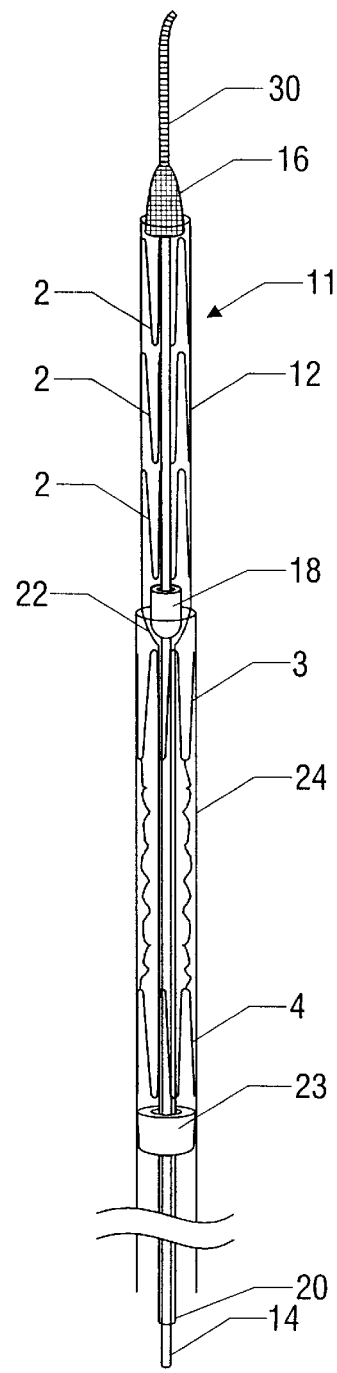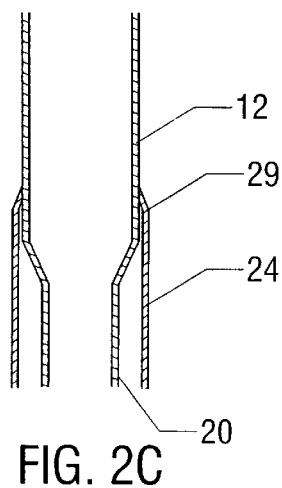
FIG. 2A
FIG. 2B
FIG. 2C
FIG. 2D

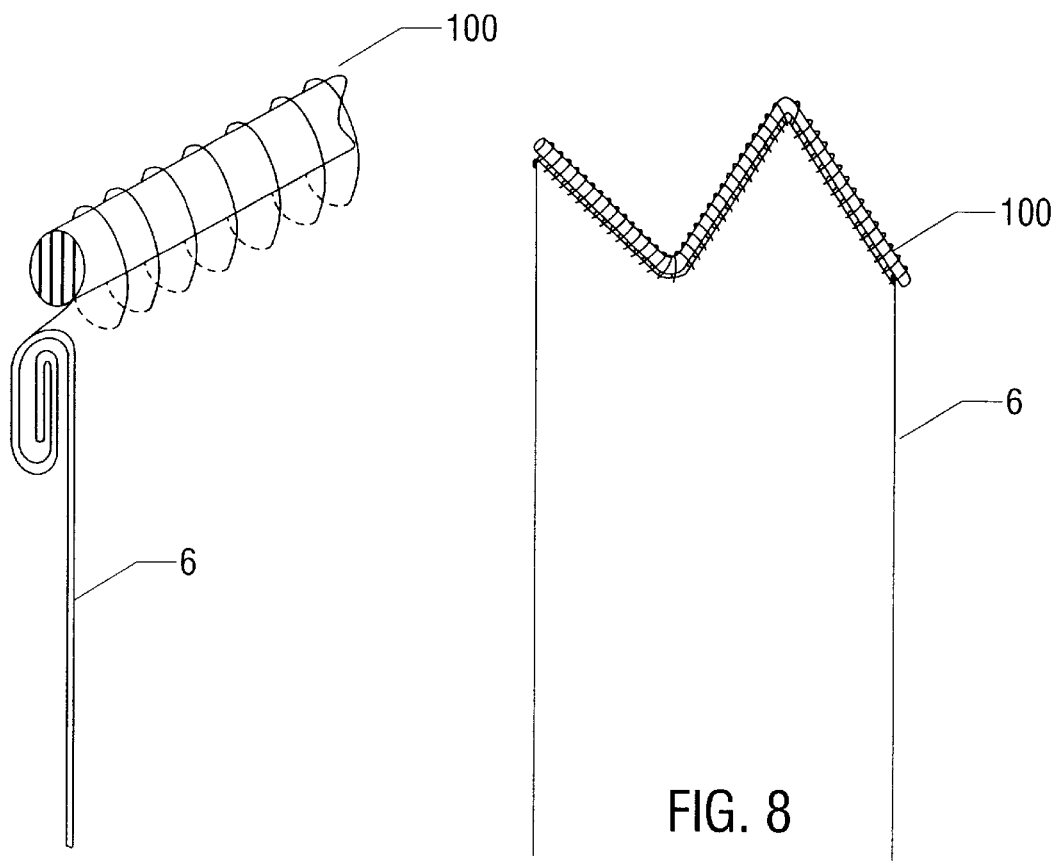
FIG. 7
FIG. 8
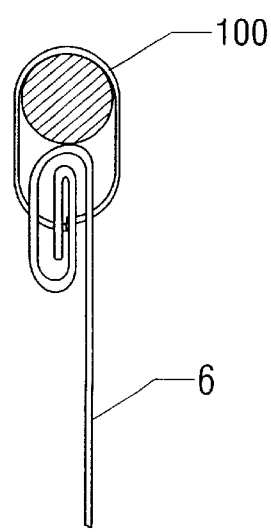
FIG. 9

DELIVERY SYSTEM AND METHOD FOR DEPOLYMENT AND ENDOVASCULAR ASSEMBLY OF MULTI-STAGE STENT GRAFT

The present application claims the benefit of U.S. Provisional Application Ser. No. 60/076,383 filed Feb. 26, 1998. The entire text of the above-referenced disclosure is specifically incorporated by reference herein without disclaimer.

BACKGROUND OF THE INVENTION

1. Field of the Invention

The present invention relates to the area of blood vessel graft systems in general. More particularly, this invention provides a catheter base deployment system for multi-layered stent grafts comprising multiple coaxial delivery mechanisms. By using the coaxial delivery mechanism system, the multiple layers of the stent graft can be assembled endovascularly.

2. Description of Related Art

Aortic aneurysms are a common type of deteriorating disease caused by weakening of the wall of a blood vessel. The weakened wall, under the pressure of flowing blood, balloons outward. Such a deformity in the wall of a blood vessel not only affects its ability to conduct blood, but also is potentially fatal if a rupture occurs at the site of the aneurysm.

Traditionally, the treatment for aneurysms entailed removing part or all of the aneurysm and implanting a replacement prosthetic section into the lumen. Alternatively, a synthetic or biomaterial graft is sutured end-to-end completely replacing the excised portion of the blood vessel. However, surgical treatment or removal of the aneurysm involves significant invasive techniques, extended hospitalization and associated risk of complications. Complications include extensive blood loss, respiratory tract infections, wound infections, and renal failure. In addition, the mortality rates (8%) are significant for such surgeries.

A more contemporary method of treatment of aneurysms is to place a graft within the lumen of the weakened blood vessel via a catheter-based device. Conventional tubular aortic replacement sections, however, are generally larger in diameter than the femoral artery, and therefore cannot be inserted through the lumen of the femoral artery. The basic concept of a translumenal placement of an endovascular prosthesis for decreasing risk associated with the surgical repair of aortic aneurysms was first experimentally investigated by Balko (J. Surg Res 1986; 40:305–09). Since then, several investigators have studied the feasibility of different endovascular devices. For example Lazarus (U.S. Pat. No. 5,669,936) discloses a graft system having a capsule catheter that is deployed after femoral arteriotomy. To date, stent-grafts used clinically for treatment of abdominal and thoracic aortic aneurysms have required large, 18-F to 30-F delivery systems. The large size of the delivery system necessitated surgical femoral artenotomy, and sometimes retroperitoneal left iliac arteriotomy or distal aorta aortotomy, igeneral anesthesia, and high levels of multidisciplinary cooperation. Occasionally, relatively healthy iliac vessels with large diameters are needed in patients with highly sclerotic tortuous iliac arteries; angioplasty with or without stenting was necessary for performance of endovascular grafting. None of the clinically used devices is suitable for percutaneous insertion; all require a femoral arteriotomy because of their size.

Recently, a catheter-based system for the delivery of grafts for repair of aortic aneurysms was disclosed by Taheri et al. (U.S. Pat. No. 5,713,917 and U.S. Pat. No. 5,591,195). The system includes a single stage graft comprised of two nitinol springs. The two nitinol springs are in physical communication with each other via a nitinol connecting bar and are embedded in graft material at each end and covered completely by material so as to prevent direct exposure to bodily fluids or tissues. The graft is deployed by using an elongated sheath introducer having an axially extending sheath passage for receiving the graft and maintaining it in a compressed condition. A flexible push rod around the insertion catheter and within the sheath passage is used to push the graft out of the sheath during deployment.

In theory, one way to decrease the size of an endovascular device is to deploy the stent graft as separate parts. However, none of the delivery devices available are suitable for delivery of a multi-stage stent graft by a single percutaneous insertion. There is thus ongoing need for graft delivery devices for treatment of aneurysms which require minimal preparation and hospitalization.

SUMMARY OF THE INVENTION

In one aspect, the invention is an apparatus for delivering a stent graft having first and second stages and includes a first sheath and a second sheath. The first sheath has a first portion configured to enclose the first stage. The first sheath has a second portion smaller than the first portion. The second sheath is configured to enclose the second portion of the first sheath. The second sheath is configured to enclose the second stent.

In other aspects, the apparatus may also include a pusher wire, having an end, configured to fit within the first sheath. The apparatus may also include a catheter configured to enclose the second portion of the first sheath. The catheter may be configured to fit within the second sheath. The apparatus may also include a tip coupled to the end of the pusher wire. The tip may be configured to facilitate manipulation of the system within a vessel. The apparatus may also include a first blocking piece coupled to the pusher wire in spaced relation with the end of the pusher wire and a second blocking piece coupled to the pusher wire between the end of the pusher wire and the first blocking piece. The first sheath may include one contiguous piece. The apparatus may also include one or more fluid openings defined in the second portion of the first sheath. The apparatus may also include a blocking piece coupled to the second portion of the first sheath in a location, the location being such that the blocking piece is positioned within the second sheath during operation of the apparatus. The apparatus may also include a microtubing configured to fit within the first sheath, the microtubing having an end. The apparatus may also include a guiding mechanism in operative relation to the end of the microtubing, the guiding mechanism being configured to facilitate manipulation of the system within a vessel. The guiding mechanism may include a guidewire configured to fit within the microtubing. The guiding mechanism may include a tip coupled to the end of the microtubing.

In another aspect, the invention is a stent graft delivery system including a pusher wire having an end, a tip, a first blocking piece, a first sheath, and a second sheath. The tip is coupled to the end of the pusher wire and configured to facilitate manipulation of the system within a vessel. The first blocking piece is coupled to the pusher wire in spaced relation with the end of the pusher wire. The first sheath is configured to enclose the pusher wire. The first sheath has a first portion configured to enclose the first blocking piece. The first sheath also has a second portion smaller than the first portion. The second sheath is configured to enclose the second portion of the first sheath.

In other aspects, the system may also include a catheter configured to enclose the second portion of the first sheath. The catheter may be configured to fit within the second sheath. The system may also include a second blocking piece coupled to the second portion of the first sheath in a location, the location being such that the second blocking piece is positioned within the second sheath during operation of the apparatus. The second blocking piece may be coupled to the pusher wire between the tip and the first blocking piece. The first sheath may include one contiguous piece. The system may also include an inner stage, an outer stage, and a graft material. The inner stage may be configured to be compressed so as to fit within the first portion of the first sheath. The inner stage may have a plurality of radially compressible spring stents connected by connecting bars. The outer stage may be configured to be compressed so as to fit within the second sheath. The outer stage may have two radially compressible spring stents connected by a connecting bar. The graft material may enclose the outer stage and may be coupled to the outer stage such that a portion of one of the two radially compressible spring stents of the outer stage may contact a vessel upon delivery of the outer stage into the vessel. The inner and outer stages may each be formed from a single wire. The graft material may be polyester. The system may also include a self-expanding tube stent configured to be constrained so as to fit within the first portion of the first sheath. The system may also include a self-expanding tube stent configured to be constrained so as to fit within the second sheath. The system may also include one or more fluid openings defined in the second portion of the first sheath.

In another aspect, the invention is a delivery system for inserting and releasing a stent graft having first and second stages into a vessel, and the system includes a first means for releasing the first stage into the vessel and a second means for releasing the second stage into the first stage. The second means is positioned so as to be inserted into the vessel before the first means is inserted into the vessel.

In other aspects, the first means may include a first sheath. The second means may include a second sheath. The second means may include a second sheath having a first portion having a first caliber. The second sheath may also have a second portion having a second caliber, the second caliber being smaller than the first caliber. The second sheath may be formed from one contiguous piece. The first means may also include a catheter for holding the first stage in position during delivery thereof, the catheter being in operative relation with the first sheath. The system may also include one or more fluid openings defined in the second portion of the second sheath. The first stage may include two radially compressible spring stents connected by a connecting bar, and a graft material for enclosing the first stage. The graft material may be coupled to the first stage such that a portion of one of the two radially compressible spring stents of the first stage may contact a vessel upon delivery of the first stage into the vessel. The second stage may include a plurality of radially compressible spring stents connected by connecting bars. The first stage may be a self-expanding tube stent. The second stage may be a self-expanding tube stent.

In another aspect, the invention is a stent graft delivery system including a pusher wire having an end, a tip, a first blocking piece, a second blocking piece, a first sheath, a second sheath, and a catheter. The tip is coupled to the end of the pusher wire and is configured to facilitate manipulation of the system within a vessel. The first blocking piece is coupled to the pusher wire in spaced relation with the end of the pusher wire. The second blocking piece is coupled to the pusher wire between the end of pusher wire and the first blocking piece. The first sheath is configured to enclose the pusher wire. The first sheath has a first portion configured to enclose the first blocking piece. The first portion has a first caliber. The first sheath also has a second portion having a second caliber smaller than the first caliber. The second sheath is configured to enclose the second portion of the first sheath. The catheter is configured to enclose the second portion of the first sheath. The catheter is also configured to fit within the second sheath.

In another aspect, the invention is a method for endovascularly assembling a stent graft having an inner stage enclosed by a leading sheath and an outer stage enclosed by a trailing sheath. The inner stage and the outer stage is inserted into a vessel, the stages being positioned such that the inner stage is inserted into the vessel before the outer stage is inserted into the vessel. The outer stage is positioned within the vessel. The outer stage is released. The inner stage is withdrawn so as to position it within the outer stage. The inner stage is released into the outer stage so as to endovascularly assemble the stent graft.

In other aspects, the step of releasing the outer stage may include pulling back the trailing sheath so as to release the outer stage. The step of releasing the inner stage may include pulling back the leading sheath so as to release the inner stage. The vessel may be an aorta, an iliac artery, an inferior vena cava, or a superior vena cava. The step of inserting may include inserting the inner stage and the outer stage into an aorta in a single percutaneous insertion in a femoral artery.

In another aspect, the invention is a method of endovascularly assembling a stent graft in an aorta. An inner and outer stage are provided. The stages are inserted into the aorta in a single percutaneous insertion through a femoral artery. The stages are positioned within the aorta, the inner stage being located cephalad of the outer stage. The outer stage is released. The inner stage is positioned within the outer stage. The inner stage is released into the outer stage so as to endovascularly assemble the stent graft.

In another aspect, the invention is a stent graft delivery system including a microtubing having an end, a guiding mechanism, a first blocking piece, a first sheath, a second sheath, and a catheter. The guiding mechanism is in operative relation to the end of the microtubing and is configured to facilitate manipulation of the system within a vessel. The first blocking piece is coupled to the microtubing in spaced relation with the end of the microtubing. The first sheath is configured to enclose the microtubing. The first sheath has a first portion configured to enclose the first blocking piece. The first portion has a first caliber. The first sheath also has a second portion having a second caliber smaller than the first caliber. The second sheath is configured to enclose the second portion of the first sheath. The catheter is configured to enclose the second portion of the first sheath. The catheter is configured to fit within the second sheath.

In other aspects, the guiding mechanism may include a guidewire configured to fit within the microtubing. The guiding mechanism may include a tip coupled to the end of the microtubing. The microtubing may be made of nitinol. The first sheath may include one contiguous piece. The system may also include an inner stage, an outer stage, and a graft material. The inner stage may be configured to be compressed so as to fit within the first portion of the first sheath. The inner stage may have a plurality of radially compressible spring stents connected by connecting bars. The outer stage may be configured to be compressed so as to fit within the second sheath. The outer stage may have two radially compressible spring stents connected by a connecting bar. The graft material may enclose the outer stage. The graft material may be coupled to the outer stage such that a portion of one of the two radially compressible spring stents of the outer stage may contact a vessel upon delivery of the outer stage into the vessel. The inner and outer stages may each be formed from a single wire. The graft material may be polyester. The system may also include a self-expanding tube stent configured to be constrained so as to fit within the first portion of the first sheath. The system may also include a self-expanding tube stent configured to be constrained so as to fit within the second sheath. The system may also include one or more fluid openings defined in the second portion of the first sheath. The system may also include a second blocking piece coupled to the microtubing between the first blocking piece and the end of the microtubing.

In another aspect, the invention is a stent graft delivery system including a microtubing having an end, a guiding mechanism, a first blocking piece, a first sheath, a second sheath, and a second blocking piece. The guiding mechanism is in operative relation to the end of the microtubing and is configured to facilitate manipulation of the system within a vessel. The first blocking piece is coupled to the microtubing in spaced relation with the end of the microtubing. The first sheath is configured to enclose the microtubing. The first sheath has a first portion configured to enclose the first blocking piece. The first portion has a first caliber. The first sheath also has a second portion having a second caliber smaller than the first caliber. The second sheath is configured to enclose the second portion of the first sheath. The second blocking piece is coupled to the second portion of the first sheath in a location, the location being such that the second blocking piece is positioned within the second sheath during operation of the system.

In other aspects, the guiding mechanism may include a guidewire configured to fit within the microtubing. The guiding mechanism may include a tip coupled to the end of the microtubing. The microtubing may be made of nitinol. The first sheath may include one contiguous piece. The system may also include one or more fluid openings defined in the second portion of the first sheath. The system may also include a third blocking piece coupled to the microtubing between the first blocking piece and the end of the microtubing.

In another aspect, the invention is a method for endovascularly assembling a stent graft. An inner stage, an outer stage, and a stent graft delivery system are provided. The stages are assembled within the delivery system. The delivery system is inserted into a vessel, the stages being positioned within the delivery system such that the inner stage is inserted into the vessel before the outer stage is inserted into the vessel. The delivery system is positioned within the vessel. The outer stage is released. The delivery system is positioned such that the inner stage is within the outer stage. The inner stage is released into the outer stage so as to endovascularly assemble the stent graft.

In other aspects, the stent graft may include a pusher wire having an end, a tip, a blocking piece, a first sheath, a second sheath, and a catheter. The tip may be coupled to the end of the pusher wire and configured to facilitate manipulation of the system within a vessel. The blocking piece may be coupled to the pusher wire in spaced relation with the end of the pusher wire. The first sheath may be configured to enclose the pusher wire. The first sheath may have a first portion configured to enclose the blocking piece. The first sheath may also have a second portion smaller than the first portion. The second sheath may be configured to enclose the second portion of the first sheath. The catheter may be configured to enclose the second portion of the first sheath. The catheter may be configured to fit within the second sheath. The step of assembling may include compressing the outer stage around the second portion of the first sheath; pulling the second sheath over the compressed outer stage and the first sheath; compressing the inner stage around the pusher wire; positioning the first sheath over the compressed inner stage; placing the pusher wire and the blocking piece into the first sheath; and placing the catheter over the second portion of the first sheath and into the second sheath. The step of releasing the outer stage may include the step of holding the catheter in place while pulling back the second sheath. The step of releasing the inner stage may include the step of holding the pusher wire stationary while pulling back the first sheath. The vessel may be an aorta, an iliac artery, an inferior vena cava, or a superior vena cava. The step of inserting may include inserting the delivery system into an aorta through a femoral artery. The stent graft delivery system may include a microtubing having an end, a guiding mechanism, a blocking piece, a first sheath, a second sheath, and a catheter. The guiding mechanism may be in operative relation to the end of the microtubing and may be configured to facilitate manipulation of the system within a vessel. The blocking piece may be coupled to the microtubing in spaced relation with the end of the microtubing. The first sheath may be configured to enclose the microtubing. The first sheath may have a first portion configured to enclose the blocking piece. The first portion may have a first caliber. The first sheath may also have a second portion having a second caliber smaller than the first caliber. The second sheath may be configured to enclose the second portion of the first sheath. The catheter may be configured to enclose the second portion of the first sheath. The catheter may also be configured to fit within the second sheath. The step of assembling may include positioning the second sheath over the outer stage; positioning the second sheath over the first sheath; placing the inner stage over the pusher wire; placing the pusher wire and the blocking piece into the first sheath; and placing the catheter over the second portion of the first sheath and into the second sheath. The step of releasing the outer stage may include the step of holding the catheter in place while pulling back the second sheath. The step of releasing the inner stage may include the step of holding the microtubing stationary while pulling back the first sheath.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is a perspective view of stage 1 of a two stage stent graft according to one embodiment of the present invention.

FIG. 1B is a perspective view of stage 2 of a two stage stent graft according to one embodiment of the present invention.

FIG. 2A is an illustration of the longitudinal section of the coaxial delivery system according to one embodiment of the present invention.

FIG. 2B is a perspective view of the pusher wire according to one embodiment of the present invention.

FIG. 2C is a cross section view of the overlap between a leading and a trailing sheath according to one embodiment of the present invention.

FIG. 2D is an illustration of another embodiment of the coaxial delivery system according to one embodiment of the present invention.

FIG. 7 is a perspective view of a graft material attached to a portion of a spring stent in a non-overlapping manner according to one embodiment of the present invention.

FIG. 8 is a front view of a graft material attached to a portion of a spring stent in a non-overlapping manner according to one embodiment of the present invention.

FIG. 9 is an end view of a graft material attached to a portion of a spring stent in a non-overlapping manner according to one embodiment of the present invention.

DESCRIPTION OF ILLUSTRATIVE EMBODIMENTS

Figure 1C:
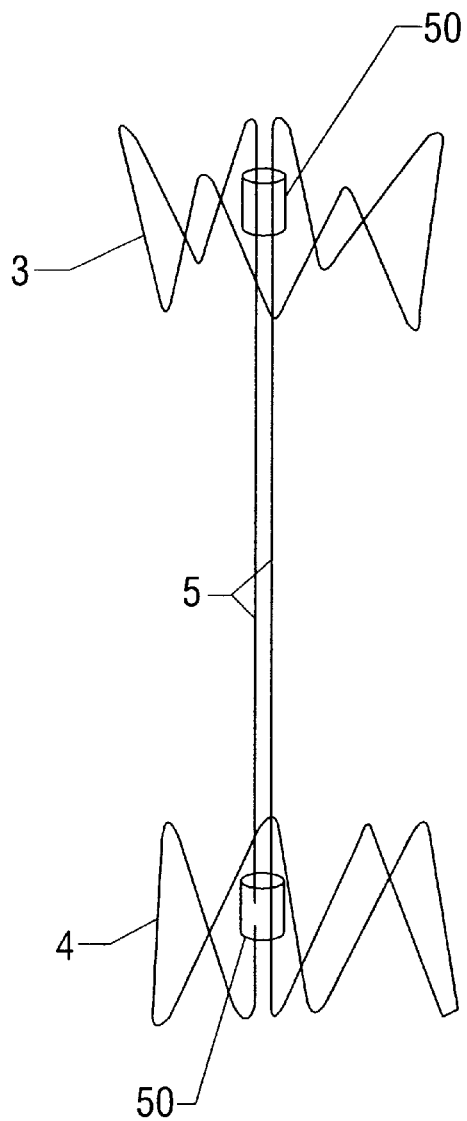
FIG. 1C is a perspective view of the metal frame of stage 1 from FIG. 1A according to one embodiment of the present invention.

Since endovascular grafting devices have to meet certain requirements of strength and durability, the possibility of reducing their size by decreasing the size of their components is limited. However, by assembling the components of the graft endovascularly, the size of the delivery system can be reduced and the flexibility of the delivery system can be increased. Thus, the stent graft of the present invention is provided as a multi-stage stent graft. Further, a delivery system is provided for the insertion of the stent graft by a single percutaneous insertion and for the endovascular assembly of the stent graft.

As used herein, the term "pusher wire" means an elongated rod with a small diameter that may be somewhat rigid and flexible, and which may be inserted into a vessel and used to help navigate the pathway of the vessel. In addition, as a part of one of the coaxial mechanisms, and by means of an attached blocking piece (defined below) it stabilizes one of the stages (defined below) during its release.

As used herein, the term "microtubing" means a small, hollow tube that, like a pusher wire, may be somewhat rigid and flexible, and which may be inserted into a vessel and used to help navigate the pathway of the vessel.

As used herein, the term "guidewire" means an elongated rod designed to allow the safe introduction of the delivery system to the vasculature, and which may be inserted into a microtubing.

As used herein, the term "blocking piece" means a small device that may be attached to a pusher wire or a microtubing, and which may fit within a sheath (defined below) and may contact a stage (defined below) of a stent graft (defined below) that is placed within the sheath so as to support, push, or pull the stage during insertion of the stage and delivery of the stage into a vessel or another stage.

As used herein, the term "sheath" means a hollow tube or cover that may be placed around objects such as pusher wires, microtubings, blocking pieces attached to a pusher wire or a microtubing, stages of a stent graft, catheters (defined below), or other smaller sheaths, and which may enclose the object and prevent the object from contacting the vessel into which the object is placed.

As used herein, the term "catheter" means, like a sheath, a hollow tube or cover that may be placed around objects such as pusher wires, microtubings, blocking pieces attached to a pusher wire or a microtubing, stages of a stent graft, sheaths, or other smaller catheters, and which may enclose the object and prevent the object from contacting the vessel into which the object is placed.

As used herein, the term "tip" means a small piece of material that may be angled and may be somewhat flexible, and that may be placed on the end of a pusher wire or a microtubing that first enters a vessel, and may serve to help control the direction of the pusher wire or the microtubing within the vessel.

As used herein, the term "guiding mechanism" means any suitable structure that may be configured to facilitate manipulation within a vessel or enclosure. Guiding mechanism may include, but are not limited to, tips and guidewires.

As used herein, the term "stent graft" means a small, hollow, compressible tubular medical device that is designed to be placed within a vessel having a weakened vessel wall so as to repair the damaged section of the vessel by providing a new passageway through which blood or other matter may flow. Stent grafts may consist of multiple layers or stages (defined below) which may be endovascularly assembled to form the stent graft.

As used herein, the term "stage" means a layer of a stent graft which may have an elastically deformable frame capable of being compressed or constrained, covered with a sheath, inserted into a vessel and then released into the vessel or into another stage so as to substantially return to its uncompressed or unconstrained form.

As used herein, the term "graft material" means a cover or jacket that may be placed around and attached to a stage so as to create a passageway through which blood or other material may flow.

As used herein, the term "self-expanding tube stent" means a small, hollow, elongated medical device having an elastically deformable structure that may serve as a stage.

As used herein, the term "radially compressible spring stent" means a small elastically deformable spring formed from a wire that is bent several times and which may serve as a stage or a portion of a stage.

As used herein, the term "endovascular" means within a vessel.

As used herein, a device that is inserted into a vessel in a "single percutaneous insertion" is placed within the vessel following one small insertion or puncture of the vessel without using surgical methods such as cut-down or arteriotomy. to the drawings, as illustrated in FIG. 1A, stage 1 of the two stage stent graft, termed the anchoring stent or the outer stage, comprises a tubular graft formed by a plurality of radially compressible spring stents preferably in the form of serpentine stents. The radially compressible spring stents are physically connected to each other by one or more longitudinal bars. Th e use of radially compressible spring stents advantageously allows stage 1 to be configured to be compressed so as to fit within the sheaths which may be utilized in delivering stage 1 (discussed below). The spring means and the connecting bars can be made as separate units or as a single unit made from a single wire. In one embodiment, stage 1 comprises two, 4–6 bend serpentine stents 3 and 4 connected by connecting bar 5. As shown in FIG. 1A, 6 bends a reused to form 6 fingers 3a on serpentine stent 3, and 5 bends are used to form 5 fingers 4a on serpentine stent 4. It is to be understood that as few as 3 bends, and as many as 10 bends, including 4, 5, 6, 7, 8, or 9 bends, may be used to form serpentine stents 3 and 4. Serpentine stent 3 is located close to one end of the graft while serpentine stent 4 is located close to the other end. In one embodiment, the use of radially compressible spring stents advantageously allows stage 1 (and stage 2, to be discussed below) to be configured to be compressed so as to fit within the sheaths which may be utilized in delivering the stages as below discussed.

Advantageously, by using a single wire to form the anchoring stent, the costs and time associated with connecting the two serpentine stents together with connecting bar 5, formed from a separate wire, may be eliminated.

Further, it is preferable to have the anchoring serpentine stents and the connecting bar made of the nickel-titanium alloy, nitinol. Nitinol is a biologically inert alloy which possesses special shape-memory properties. The alloy is made of approximately equal amounts of nickel and titanium. The shape-memory properties of nitinol allow the wire coil springs which are initially fabricated with a desired shape and configuration to be reshaped into a temporary compressed configuration, which is more suitable for transluminal placement. The alloy typically is stable at room and body temperature, but can be forced to lose its malleability and permanently revert to its initially fabricated configuration. The transition temperature of the alloy can be controlled by varying its composition and processing. For example, annealing the stage at 500 degrees Celsius for 5 to 15 minutes, preferably 12 to 15 minutes, may impart the alloy with superelastic properties. At this same temperature, heating the alloy for 60 to 120 minutes, preferably 90 to 120 minutes, may impart the alloy with temperature-dependent thermal-shape memory, which may advantageously allow it to be malleable at room temperature.

Figure 1D:
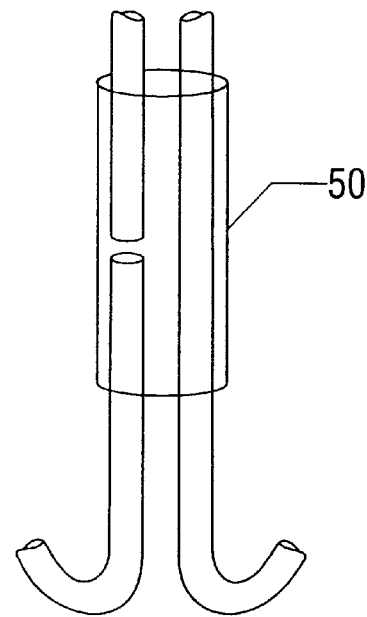
FIG. 1D is a magnified view of a portion of the metal frame in FIG. 1C showing the use of a single nitinol wire for creating the metal frame according to one embodiment of the present invention.

The anchoring stent graft is enclosed by graft material 6 and the serpentine stents may, for example, be stitched thereto with multiple stitches 7. As illustrated in FIG. 1C and FIG. 1D, the unit can be made from one nitinol wire forming both the anchoring serpentine stents and the connecting bar(s). As further illustrated in FIG. 1C and 1D, when a single wire is used to form stage 1, portions of the wire may be supported or reinforced by pieces 50. Pieces 50 may be hollow pieces through which the wire is threaded during the shaping of the stent, bearing any feasible shape such as a cylinder, oval, triangle or rectangle. In another embodiment, pieces 50 may be flat pieces the ends of which are bent around the portions of the wire being supported or reinforced. Pieces 50 may be made from any suitable material such as nitinol or stainless steel, and may be attached to the relevant portions of the wires by any suitable means such as welding, crimping, and the like.

In one embodiment of the present invention, when a single wire is used to form stage 1, the wire may have different caliber segments. For example, the caliber of the portion(s) of the single wire forming connecting bar(s) 5 may be larger than the caliber of the portions of the single wire forming the serpentine stents 3 and 4. As a result, the rigidity of the connecting bar(s) 5 may be increased, thereby increasing the likelihood that stage 1 will maintain its shape as it is being released into a vessel as below described. This variation in caliber may be achieved, for example, by purchasing the wire from the manufacturer thereof in the desired configuration, or by physically removing portions from the wire using any suitable means such as chemical etching, and the like. Similarly, the portions of the wire which are supported or reinforced by pieces 50 may be decreased in caliber so as to reduce the profile of stage 1 without jeopardizing the mechanical integrity of stage 1.

Figure 4:
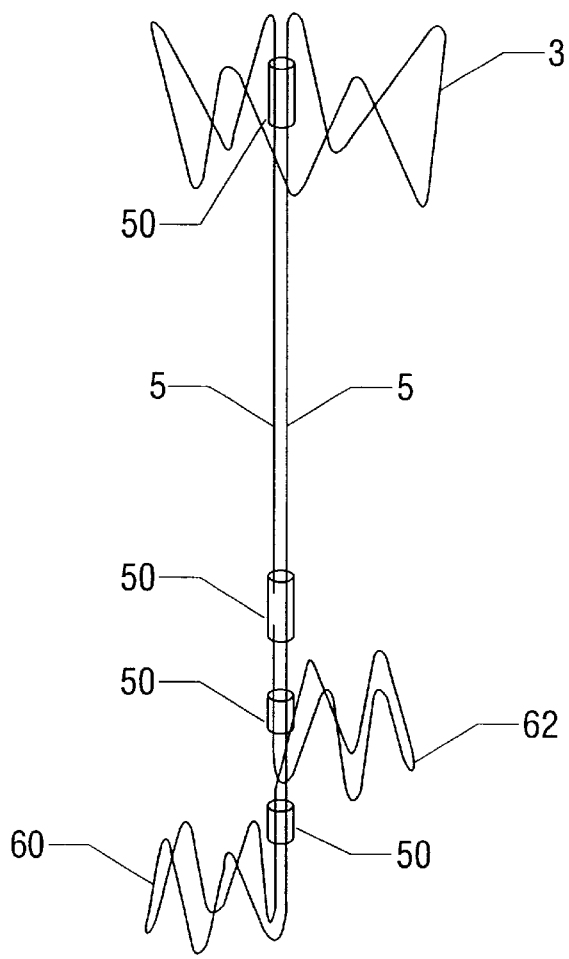
FIG. 4 is a perspective view of a bifurcated frame of stage 1 of a two stage stent graft according to one embodiment of the present invention.
Figure 19:
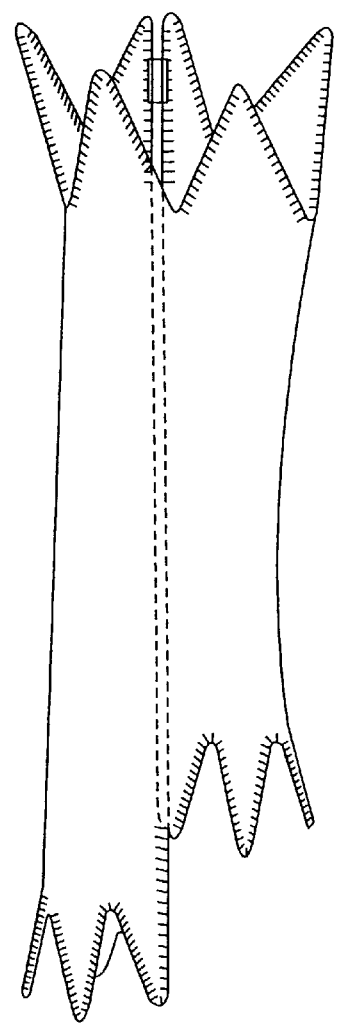
FIG. 19 is a perspective view of a bifurcated stage 1 of a two stage stent graft according to one embodiment of the present invention.

As shown in FIG. 4, in another embodiment of the present invention, stage 1 may be formed from a single wire and have a bifurcated shape such that the distal end of stage 1 comprises two serpentine stents with a smaller unconstrained profile than the serpentine stent at the proximal end. These three serpentine stents may also be formed from separate wires. As shown in FIG. 4, the single wire used begins and ends near the distal end of stage 1. It is to be understood, however, that the wire may begin and end at different locations. Stage 1, as shown in FIG. 4, was formed by first extending the wire as connecting bar 5 and forming the proximal larger profile serpentine stent 3. Then the wire returns as the other connecting bar 5 and forms the right serpentine stent 60, and then forms the left serpentine stent 62. The left serpentine stent may be positioned above the right serpentine stent, as shown, so that the two smaller serpentine stents do not overlap when they are compressed and inserted into or are enclosed by a sheath as below described. As a result, stage 1 maintains a smaller constrained profile within a delivery sheath than if the two small serpentine stents did overlap. Pieces 50 may be used to reinforce the integrity of the design as shown. Graft material may be attached to this embodiment of stage 1, by any suitable means as below described. For example, FIG. 19 shows bifurcated stage 1 covered by graft material using stitches.

The graft material for the stent graft of the present invention is chosen so that the graft is capable of substantially deforming to conform to an interior surface of a blood vessel. Suitable synthetic materials include, but are not limited to, woven polyester, polytetrafluoroethylene (PTFE), microporous urethane, nylon, and lycra. A preferred fabric material is thin polyester. Graft material that is minimally porous, or even nonporous may be utilized. For example, a material such as PeCap® polyester (commercially available from Tetko, Inc., Briarcliff Manor, N.Y.) having a pore size of 5 micron, a fabric thickness of 65 micron, and an open area of 2 percent may be used. In one embodiment of the invention, a photopolymerization technique is used to treat the polyester. While not intending to be bound by any theory, it is believed that photopolymerization makes the surface of the polyester conducive to bonding of proteins which is necessary to create a collagen rich surface. This would enable a thinner, higher porosity fabric to be utilized without bleed-through and also would promote healing. In addition, cryogenically preserved biological materials, for example, veins including umbilical cord veins, also can be used. Further, the selection of the material may depend upon the site of implantation. For example, polyester (Dacron) may be more suitable for aortic wall which experiences a higher pressure change than for example, iliac artery, where PTFE is the preferred material.

Figure 24:
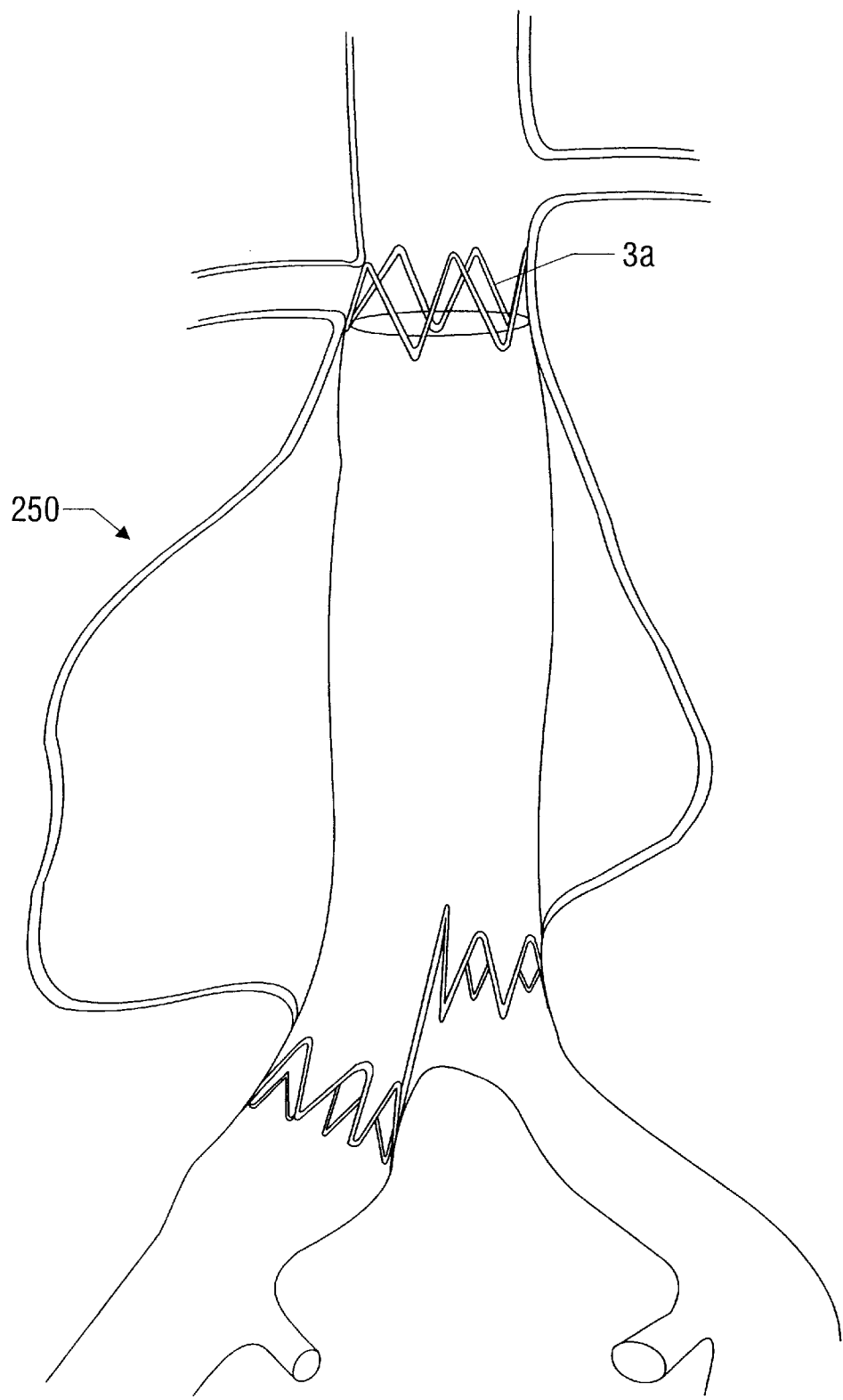
FIG. 24 is a perspective view of a stent graft delivered in an abdominal aortic aneurysm according to one embodiment of the present invention.

The position of the graft material on the anchoring stent may be affected by the location of the damage to the vessel. For example, due to the short proximal infrarenal neck of the abdominal aortic aneurysm 250 shown in FIG. 24, the aneurysm may be stent grafted such that the fingers 3*a* of the anchoring stent are positioned in the renal flow. As renal flow should not be impeded, the graft material may be attached to the anchoring stent using any suitable means described below such that fingers 3*a* are left substantially uncovered.

As shown in FIG. 1B, the second part, stage 2 of the two-stage stent graft termed the scaffolding stent or the inner stage is also made of a plurality of radially compressible spring stents 9 connected by connecting bars 8. As with stage 1, the use of radially compressible spring stents advantageously allows stage 2 to be configured to be compressed so as to fit within the sheaths which may be utilized in delivering stage 2 (discussed below). In one embodiment, stage 2 fits longitudinally between the serpentine stents 3 and 4 of stage 1. In another embodiment, to achieve a reliable seal between the vessel wall and the edges of the graft material enclosing the anchoring stent, stage 2 may be delivered or released into stage 1 such that the scaffolding stent overlaps either or both serpentine stents of the anchoring stent. By doing so, the expansile or radial force of the scaffolding stent coupled with the expansile force of the serpentine stents of the anchoring stent may help to avoid any leak from the newly formed lumen of the stent graft into the aneurysmal sac. Although 3 spring stents are shown in FIG. 1B, it is to be understood that in another embodiment of the present invention, as few as one spring stents or as many as 12, or any number therebetween, may be used to make up the scaffolding stent.

Figure 1E:
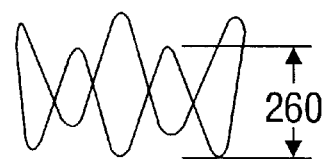
FIG. 1E is a perspective view depicting the height of a spring stent according to one embodiment of the present invention.

Stage 2 may be made as a whole of one coherent element using only one wire or may be made of separate elements. If made from a single wire, the advantages discussed above may be achieved. In a preferred embodiment, the spring stents and the connecting bar(s) are made of nitinol. The unit may be bare or may be enclosed in coverings made of thin polyester. While not intending to be bound by any particular theory, it is believed that covering the stent graft with a thin polyester covering will decrease the permeability of the stent graft for abdominal aortic aneurysm treatment. Further, when a covering is used, the covering may add to the rigidity of the scaffolding stent, thereby decreasing the likelihood that the separate spring stents (if more than one is used) will cram into each other as the scaffolding stent is being delivered as below described. In one embodiment illustrated in FIG. 1B, the unit is bare and made of 4–6 bends of nitinol wire serpentine stents. In another embodiment, the number of bends used in forming the spring stent or stents of the scaffolding stent may be similar to the number of bends used in forming the spring stents of the anchoring stent above discussed. Further, it is to be understood that the number of bends may be decreased in a given spring stent while retaining the radial or expansile force of the spring stent by utilizing a larger caliber of wire. Additionally, the expansile force of a given spring stent may be increased by decreasing the height 260 of the bend, shown in FIG. 1E. The stent bodies are connected to each other with nitinol Bar 8. It is important to note that neither the anchoring stent 1, nor the inner scaffolding stent 2, are equipped with barbs.

Figure 5A:
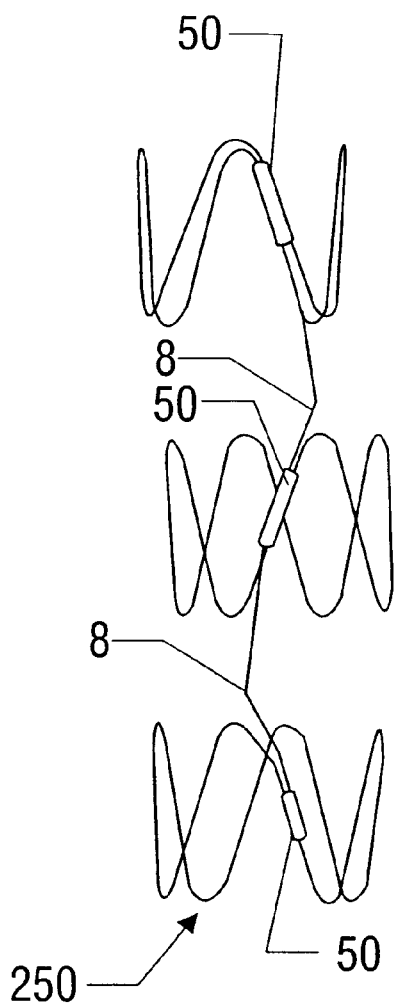
FIGS. 5A and 5B are perspective views depicting different configurations of stage 2 of a two stage stent graft according to one embodiment of the present invention.
Figure 5B:
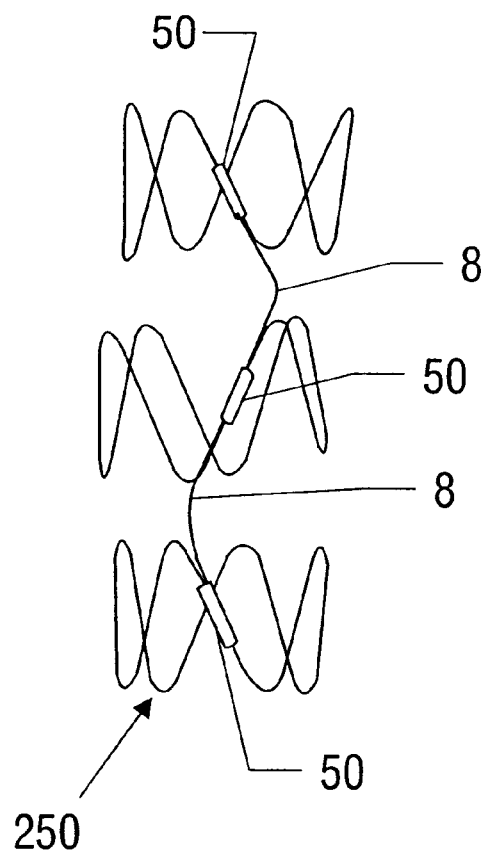

As shown in FIGS. 5A and 5B, the scaffolding stent 2 may be formed from one wire. FIGS. 5A and 5B show two possible shapes for scaffolding stent 2. As shown in these figures, the connecting bars 8 may be bent slightly, and pieces 50 may be utilized to support the scaffolding stent at locations where portions of the wire are positioned sideby-side. As shown, the connecting bars are formed on one side of the scaffolding stent.

In one embodiment of the present invention, stages 1 or 2 may be formed from self-expanding tube stents, including both slotted tube designs such as the MEMOTHERM stent (commercially available from CR Bard), and woven wire mesh stents, such as the stent shown in U.S. Pat. No. 4,655,771 to Wallsten (1987) (commercially available from Schneider/Boston Scientific), or the SYMPHONY stent (commercially available from Boston Scientific). Advantageously, the nature of self-expanding tube stents is such that they are configured to be constrained so as to fit within the sheaths (discussed below), and then may be released into a vessel, or into other stages. These stents may be covered, for example, by treating the stents with a solvent and then dipping them into a polyurethane bath for an appropriate period of time to form a polyurethane cover thereon, a procedure well known in the art. Graft materials that are able to follow the movement of the wires making up the tube stents when the tube stents are compressed and/or elongated and do not hinder the movement of the wires, such as stretchable ultra-thin polyester fabric, may also be used. Such graft materials may be attached to the stents using monofilament sutures as below described. At least one of the stages of a multi-stage stent graft formed using self-expanding tube stents should be covered.

Radiopaque markers may be placed along the stages in a manner well-known in the art, to enable the operator to better view the stages using fluoroscopy.

In one embodiment of the invention, the stent graft comprises three stages. The total thickness of the graft material will depend upon the requirements. In one embodiment, the total thickness of the material is 0.18 mm with each layer of material being 0.06 mm thick. The first stage has serpentine stents at the top and bottom of the graft connected by a connecting bar. The second stage has multiple serpentine stents connected by a connecting bar. In one embodiment, the longitudinal dimensions of the second stage are such that when deployed within the first stent, the second stent fits into the space between the upper and the lower serpentine stents of the first stage. In another embodiment, the longitudinal dimensions of the second stage may be such that when deployed within the first stage, the serpentine stents of the second stage overlap those of the first stage, thereby decreasing the potential for leakage of blood into the aneurysmal sac formed between the exterior of the covering material of stage I and the stretched, weakened wall of the aneurysm.

In one embodiment, the distance between each of the five serpentine stents in the assembled stage one and stage two unit is approximately 5 mm. The third stage of the stent graft is similar to the first stage with serpentine stents at the top and bottom. The third stage may be placed within the first and second stage so as to overlap both the first and second stages. The second stage which forms the backbone of the assembled graft, may be bare or covered with fabric. The fabric covering the various stages may be made of stretchable or non-stretchable materials. Examples of suitable covering materials and methods of sewing the stents within the graft have been disclosed in U.S. Pat. No. 5,713,917 to Taheri et al., which methods are hereby incorporated by reference. In a preferred embodiment, the fabric covering the first stent in made of a stretchable material enabling the upper and lower serpentine stents to conform to the diameter of the wall of the vessel and prevent any leaks around the edges of the graft (see U.S. Pat. No. 5,713,917 to Taheri et al.). The second and the third stages are preferably made of non-stretchable material to provide strength around the area of the aneurysm. When assembled, the first stage forms the outermost layer, the second stage forms the middle layer and the third stage forms the innermost layer and is exposed to the lumen of the vessel.

As shown in FIGS. 7–9, in one embodiment of the present invention, the graft material used to cover the various stages may be attached to the appropriate portions of the wire using a non-overlap method. As shown in FIGS. 7–9, using the non-overlap method, the graft material 6 does not overlap the wire to which it is attached, and thus the profile of the stage will not be increased as would be the case if the material overlapped the wire. Thus, when graft material 6 is coupled to stage 1 using the non-overlap method, a portion of one of the two radially compressible spring stents of stage 1 may contact a vessel upon delivery of the outer stage into the vessel. As shown in FIG. 9, the cover or graft material 6 may be folded one or more times such that the thickness of the folded material is approximately as thick as or less thick than the thickness of the wire. FIG. 8 shows the folded portion of graft material 6 on the inside of the stent. As shown in FIG. 7, for example, the material may then be attached to the wire with stitches of a single monofilament suture 100 such as a 5-0, 6-0, or 7-0 polypropylene suture. Such sutures be PROLENE sutures, commercially available from Ethicon. After every 5 to 20 stitches of the continuous suture, one or more knots may be made. As a result of the knots, a mechanical failure of the suture should not result in clinically significant consequences.

In another embodiment, the first stage is formed by a hollow foamed tube. While this stage may or may not have metal stents, it is preferable to have some longitudinal support so as to avoid problems of jamming of the layer in the delivery device or its deformation upon deployment. The longitudinal support may be a nitinol wire along the length of the foamed tube. Further, it is preferable to have one serpentine stent at the top so as to enable easy release during deployment. The second stage comprises two serpentine stents; one at the top and one at the bottom, and a connecting bar. The third stage is a scaffolding stent and comprises multiple serpentine bars that will fit in between the upper and the lower serpentine stents of the second stage. The fourth stage is similar to the second stage.

In one modification of the present invention, an adhesive is coated in between the layers or stages of the stent graft. Suitable adhesives include fibrin glue and isobutyl 2 cyanoacrylate. In another embodiment of the present invention, n-butyl 2 cyanoacrylate (commercially available as Histoacryl-Blau from B. Braun, Melsungen, Germany) which is not considered carcinogenic, also may be utilized. In one illustration of the embodiment, in a two-stage or a three-stage stent, fibrin glue is coated on the external surface of the scaffolding stent. The adhesive may be released in vivo as described in U.S. Pat. No. 5,713,917, which method is hereby incorporated by reference. In a four stage stent comprising an outer foam layer, fibrin glue can also be applied to the top and bottom portions on the external surface of the foam layer so as to form a tight seal with the wall of the blood vessel. While not intending to be bound by any particular theory, it is believed that the multiple layers provide means for the ingrowth of cells from the blood vessel wall into the graft. The fibrin coating facilitates the attachment and growth of the cells thus strengthening the graft.

The multi-stage stent graft may be deployed using devices well known in the art. For example, U.S. Pat. Nos. 5,713,917 and 5,591,195 to Taheri et al. disclose methods to deploy graft to blood vessel, which methods are hereby incorporated by reference. Thus, multiple layers of the graft can be loaded in succession within the introducer sheath with a plunger dividing the various stages within the sheath. Thus, the first stage could be delivered, and then the delivery system would have to be advanced to deliver the next successive stage. The multiple stage stent grafts also may be delivered using the coaxial delivery system of the present invention. Since the stent graft is in the form of multiple stages, the size of the delivery system can be reduced so that it can be inserted percutaneously without the need for femoral arteriotomy. By using the coaxial delivery system of the present invention the multiple stages of the stent graft are assembled easily inside the blood vessel, and the entire delivery can be carried out quickly and continuously.

The various stages of the multi-stage stent graft also can be delivered separately. If delivered separately, it in preferable that the all the stages be placed without delay, otherwise thrombosis may occur between the graft material and aortic wall as well as intraluminally between the pleats of the partially expanded graft material. A clot formation may jeopardize patency of aortic side branches which is critically important for treatment of thoracic aortic aneurysms, decrease the lumen of the graft itself, and be a source of distal embolization. Recatheterization of the lumen of the graft material may be time consuming and may even cause the migration of the previously deployed part.

In the case in which multiple stages are loaded in succession within the introducer sheath, or in the case in which stages are delivered separately, special care would be required to avoid entanglement of the stages during deployment. With either method, after deploying or delivering the first stage, the delivery sheath must be repositioned by advancing it through the lumen of the previously released stage. This manipulation could result in loss of access to the lumen of the previously released stage, entanglement of the delivery sheath within the graft material of the delivered stage, or dislodgment of the delivered stage. As a result, vascular damage such as intimal laceration, penetration or perforation of the vessel, and, in the case of aneurysm, eventually rupture of the aneurysm might occur. Further, regarding a stage delivered to the cranial area, cranial dislodgement of a delivered covered stage can occlude the orifice(s) of the renal artery(ies) threatening serious consequences.

Advantageously, using the double coaxial delivery system according to the present invention, the delivery system remains in the lumen of the graft material during the entire procedure. When delivering a two-stage stent graft, there is no need to advance the delivery system through the lumen of the previously deployed or delivered stage. Positioning of the second stage as well as removal of the delivery system requires withdrawal of the delivery system. Therefore, the entire delivery can be carried out continuously and quickly, eliminating, for example, the risk of renal artery occlusion from cranial dislodgement of a previously released stage.

Furthermore, when delivering a three-stage stent graft using the double coaxial delivery system of the present invention, the delivery system must only be advanced once after the first stage is delivered or released. That is, in one embodiment of the present invention, the first stage is positioned within the vessel and then released such that the first stage engages the vessel. Then the delivery system is advanced once to position the second stage within the first stage. After being so positioned, the second stage is released into the first stage such that the second stage engages the first stage. Next, the delivery system is withdrawn to position the third stage within the second stage. After being so positioned, the third stage is released into the second stage such that the third stage engages the second stage. In another embodiment of the present invention, the first stage is released within the vessel as just described. Then, the delivery system is withdrawn to position the second stage within the first stage. After being so positioned, the second stage is released into the second stage such that the second stage engages the first stage. Next, the delivery system is advanced once to position the third stage within the second stage. After being so positioned, the third stage is released into the second stage such that the third stage engages the first stage.

In contrast, when delivering a three-stage stent graft using either of the methods above, the delivery system would have to be advanced twice after the first stage is released; once to position the second stage within the first stage, and once more to position the third stage within the second stage.

Thus, advantageously, the multiple stage stent grafts of the present invention may be delivered using the coaxial delivery systems of the present invention. Since the stent graft is in the form of multiple stages, the size of the delivery system can be reduced so that it can be inserted percutaneously without the need for femoral arteriotomy. By using the coaxial delivery system of the present invention the multiple stages of the stent graft are assembled easily inside the blood vessel, and the entire delivery can be carried out quickly and continuously.

It is to be understood that the delivery systems of the present invention, may be inserted by way of a single percutaneous insertion. The access vessel (most frequently the right femoral artery or vein) is punctured through the skin with an appropriate needle. Through the lumen of the needle, a guidewire is inserted into the body and the needle is removed. Over the guidewire, an introducer sheath may be advanced through which a delivery system utilizing a pusher wire may be advanced to the treatment site, or, in the case of a delivery system utilizing a microtubing, the microtubing and remainder of the delivery system may be advanced to the treatment site directly over the guidewire. Advantageously, procedures carried out using a single percutaneous insertion are minimally invasive and can usually be performed on an outpatient basis.

It is also to be understood that the delivery systems of the present invention may be surgically inserted into the vessel. For example, endovascular repair of a lesion whose size requires a 14-F delivery system may be suitably carried out with the delivery systems of the present invention via a femoral arteriotomy. As such, all the benefits of the present delivery systems such as flexibility and the like will be realized.

The size of the delivery system needed for placement of a self-expanding stent-graft made of serpentine (or Z-) stents is determined by several factors. One is the required amount of radial force exerted by the stents. If the radial force of the stent is increased by increasing the size of the stent wire and/or the number of bends (Fallone et al., 1986), a larger delivery system may be required because the compressed diameter of the stent would also be increased. Another factor influencing the required size of the delivery system in the diameter of the recipient vessel. To increase the unconstrained diameter of a serpentine (or Z-) stent, more terminal bends may be added which in turn increases the compressed diameter of the stent. The thickness of the covering material itself has a substantial impact on the compressed diameter of the graft and therefore the size of the delivery sheath. The amount of friction between the graft and the delivery sheath can affect the required size of the delivery system. Friction is influenced by the graft material, the radial force of the stems, and the length of the stent framework. An increase in the graft material's coefficient of friction, the radial force of the stents, and/or the length of the stent framework results in greater friction between the device and the delivery sheath which may necessitate use of a larger delivery system. Yet another factor influencing the size of the delivery system is the manner in which the delivery system is inserted into the vessel. Delivery systems that may be inserted into a vessel using surgery may be larger than those that may be inserted into a vessel in a single percutaneous insertion.

Illustrated in FIG. 2A is a double coaxial delivery system according to the present invention for delivery or implantation of a two-stage stent graft as illustrated in FIGS. 1A and 1B. Also described is a method of deployment and endovascular assembly of the two-stage graft. However, as those skilled in the art will appreciate, the invention encompasses multiple coaxial delivery systems. Referring to FIG. 2A, double coaxial system 10 of the present invention comprises two independent coaxial delivery sheaths 11 and 24. Sheath 24 is constructed for the deployment or release of stage 1 of the two-stage stent graft in FIG. 1A, while sheath 11 is for the delivery of the scaffolding stent (stage 2) of FIG. 1B, within the lumen of the anchoring stent (stage 1).

As shown in FIG. 2A, leading portion 12 of sheath 11 is preferably made of a thin walled sheath. Sheaths 11 and 24 (and 40, to be discussed below) may be constructed of any suitable material such as TEFLON (TEFLON sheaths being commercially available from Cook), NYLON, or the like. In an embodiment useful for a single percutaneous insertion, the outer diameter of leading portion 12 may be between 7-F and 14-F, and is preferably 8-F to 12-F when the delivery system enters through vessels such as femoral arteries, and even more preferably 10-F to 12-F in such cases, and is preferably 8-F to 14-F when the delivery system enters through vessels such as femoral veins, and even more preferably 10-F to 12-F in such cases, and is preferably 8-F to 10-F when the delivery system enters through vessels such as the carotid artery, and even more preferably 9-F to 10-F in such cases. In an embodiment useful for surgical insertion, the outer diameter of leading portion 12 may be between 8-F and 24-F, and is preferably 12-F to 16-F when the delivery system enters through vessels such as femoral arteries, and even more preferably 12-F to 14-F in such cases, and is preferably 12-F to 24-F when the delivery system enters through vessels such as femoral veins, and even more preferably 12-F to 16-F in such cases, and is preferably 8-F to 12-F when the delivery system enters through vessels such as the carotid artery, and even more preferably 8-F to 10-F in such cases. It is to be understood that the sizes above may differ according to the manner of insertion and the size of the vessel into which the delivery system is placed.

Figure 12:
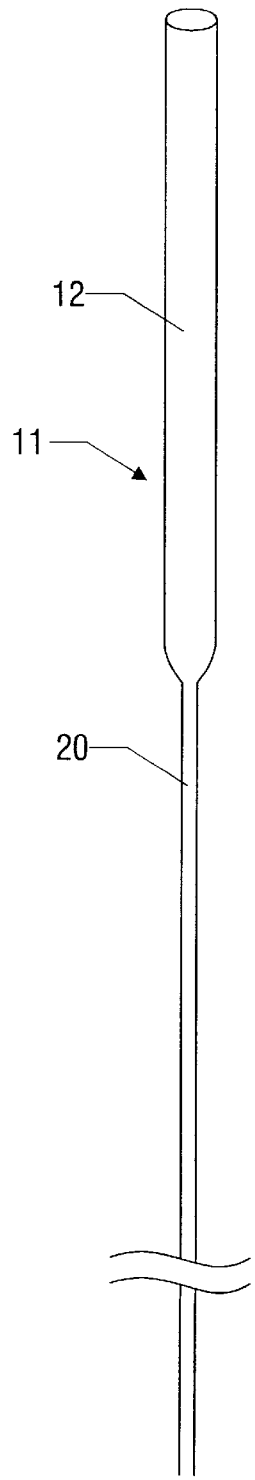
FIG. 12 is a perspective view of a sheath formed from one contiguous piece and having two differently sized portions according to one embodiment of the present invention.

The distal end of the leading portion 12 of leading sheath 11 tapers into small caliber catheter 20. In an embodiment useful for a single percutaneous insertion, the outer diameter of catheter 20 may be 2.5-F to 5-F, and is preferably 2.5-F to 4-F, and even more preferably 2.5-F to 3.5-F. In an embodiment useful for surgery, the outer diameter of catheter 20 may be 3-F to 7-F, and is preferably 3-F to 5-F, and is even more preferably 3-F to 4-F. It is to be understood that the sizes above may differ according to the method of insertion and the size of the vessel into which the delivery system is placed. Leading portion 12 may be connected to portion 20 with a tapered connecting piece 22. Connecting piece 22 may be made from materials similar to those from which sheaths 11 and 24 (and 40) may be made. The joint of the distal end of the leading portion 12 and the tapered connecting piece 22 should be strong enough to be able to withstand significant forces during delivery. In one embodiment of the present invention, leading portion 12 and small caliber catheter 20 of sheath 11 may be made from one contiguous piece, as shown in FIG. 12., thereby eliminating the joint between the two pieces.

As further shown in FIG. 2A, the scaffolding stent 2 surrounds a pusher wire 14 and is held within the leading portion 12 of the delivery system between two blocking pieces 16 and 18, located in spaced relation to one another, one distal and one proximal to the scaffolding scent. In one embodiment of the present invention, blocking piece 16 may serve to secure the scaffolding stent in position. The front portion of blocking piece 16, the portion that first enters the vessel, may also be tapered so as to provide the front portion of the delivery system with a smooth profile, thereby facilitating the intravascular travel of the delivery system. However, it is to be understood that the use of blocking piece 16 in the embodiments of the delivery system disclosed herein is optional. Thus, in one embodiment, blocking piece 16 is not coupled to pusher wire 14 (or microtubing 31, to be discussed below). In one embodiment of the present invention, blocking piece 18 serves to prevent pusher wire 14, to which it may be attached as described below, from being pulled back through sheath 11. Blocking piece 18 serves this function by contacting tapered portion 22. The portions of the blocking pieces that may contact the stents may have circular indentions for keeping the compressed bends of the stents together within the respective delivery sheaths.

Figure 10:
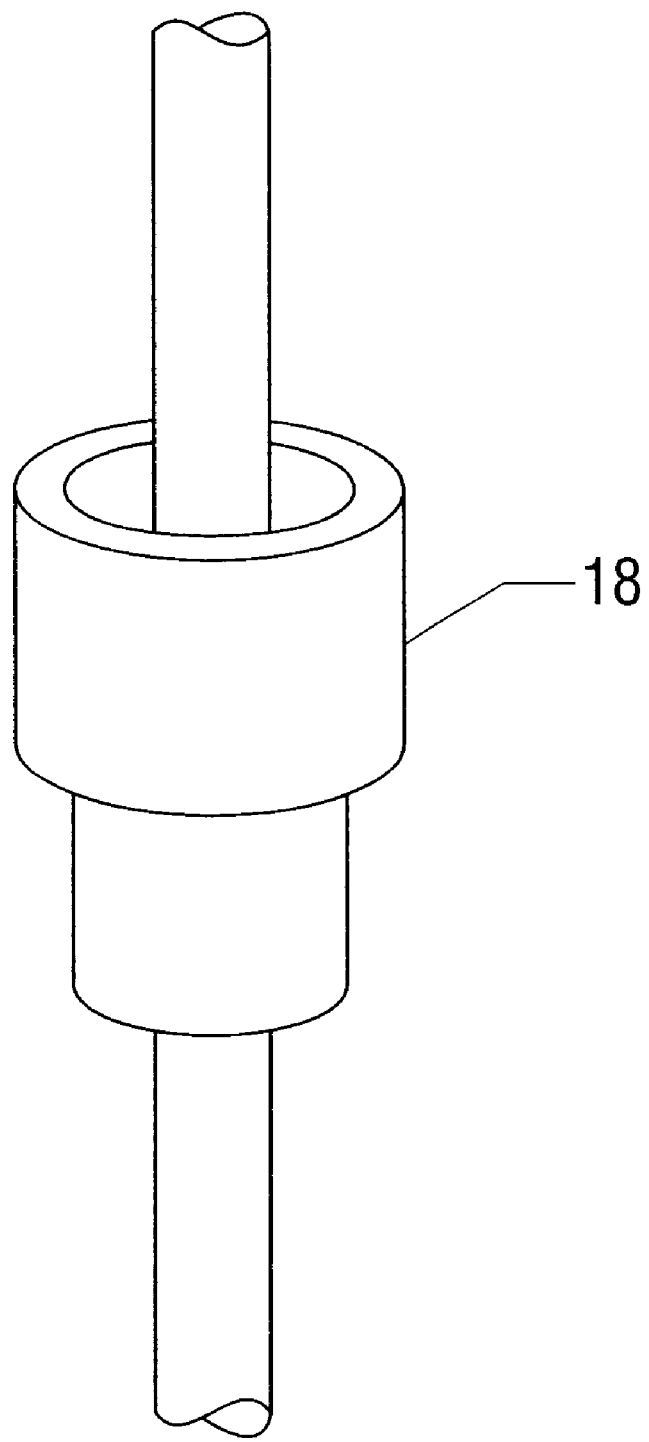
FIG. 10 is a perspective view of an adjustable plunger for use as a blocking piece according to one embodiment of the present invention.

Pusher wire 14 may be made from any suitable material such as stainless steel, nitinol, or the like. In an embodiment useful for a single percutaneous insertion, pusher wire 14 may have a diameter ranging from 0.020 inches to 0.060 inches, and is preferably 0.020 inches to 0.045 inches, and even more preferably 0.020 inches to 0.038 inches. In an embodiment useful for surgery, pusher wire 14 may have a diameter ranging from 0.020 inches to 0.080 inches, and is preferably 0.020 inches to 0.060 inches, and even more preferably 0.020 inches to 0.040 inches. It is to be understood that the sizes above may differ according to the manner of insertion and the size of the vessel into which the delivery system is placed. pieces 16 and 18 (and those discussed below) may be formed from any suitable material such as stainless steel, nitinol, plastic, or any suitable material. In one embodiment of the present invention, blocking pieces 16 and 18 may be coupled to pusher wire 14 by welding, soldering, friction fit, taping, gluing, or any suitable means. In another embodiment of the present invention, an adjustable plunger may be used for blocking piece 18, as shown in FIG. 10. Such an adjustable plunger may use a tightening screw mechanism to achieve its adjustable nature along pusher wire 14 (or microtubing 31, to be discussed below).

As shown in FIG. 2A and FIG. 2B, the front part of the pusher wire 14 is equipped with a short flexible angled tip 30 to facilitate manipulation within the vasculature. In one embodiment, tip 30 may be an angled piece of a guidewire formed from a stainless steel coil wrapped around a stainless steel core wire, and may be flexible. Tip 30 may be attached to the end of pusher wire 14 that first enters the vessel using any suitable means such as soldering, welding, gluing, taping, or the like. In another embodiment, pusher wire 14 may be tapered, and tip 30 may be a coil attached to the tapered portion of the wire, using any suitable means, such as those just described. In one such embodiment, tip 30 may be made of a highly radiopaque metal such as tungsten, platinum, or the like, or it may be made of a material such as rubber, or the like. In one embodiment, the end of tip 30 may be rounded so as to allow for smooth passage through the vasculature.

In an embodiment useful for a single percutaneous insertion, tip 30 may be 2 to 10 cm in length, and preferably 3 to 8 cm in length for use in vessels such as femoral arteries, and even more preferably 3 to 5 cm in length in such cases, and preferably 2 to 10 cm in length for use in vessels such as femoral veins, and even more preferably 3 to 8 cm in length in such cases, and is preferably 2 to 8 cm in length for use in vessels such as carotid arteries, and even more preferably 3 to 5 cm in length in such cases. In an embodiment useful surgical insertion, flexible tip 30 may be 2 to 8 cm in length, and preferably 2 to 6 cm in length for use in vessels such as femoral arteries, and even more preferably 2 to 4 cm in length in such cases, and is preferably 2 to 8 cm in length for use in vessels such as femoral veins, and even more preferably 2 to 4 cm in length in such and is preferably 2 to 8 cm in length for use in vessels such as carotid arteries, and even more preferably 2 to 4 cm in length in such cases. It is to be understood that the sizes above may differ according to the manner of insertion and the size of the vessel into which the delivery system is placed.

In an embodiment useful for percutaneous insertion, tip 30 may have an outer diameter of 0.025 inches to 0.038 inches, including 0.026, 0.027, 0.028, 0.029, 0.030, 0.031, 0.032, 0.033, 0.034, 0.035, 0.036, or 0.037 inches. In an embodiment useful for surgical insertion, tip 30 may be shorter and have a larger diameter of 0.025 to 0.080 inches, and is preferably 0.025 to 0.060 inches in diameter when a femoral artery approach is taken. It is to be understood that the sizes above may differ according to the manner of insertion and the size of the vessel into which the delivery system is placed. In an embodiment in which tip 30 is made of soft plastic, the portion of tip 30 that first enters the vessel may be tapered so as to reduce its diameter along the tapered portion.

Figure 11:
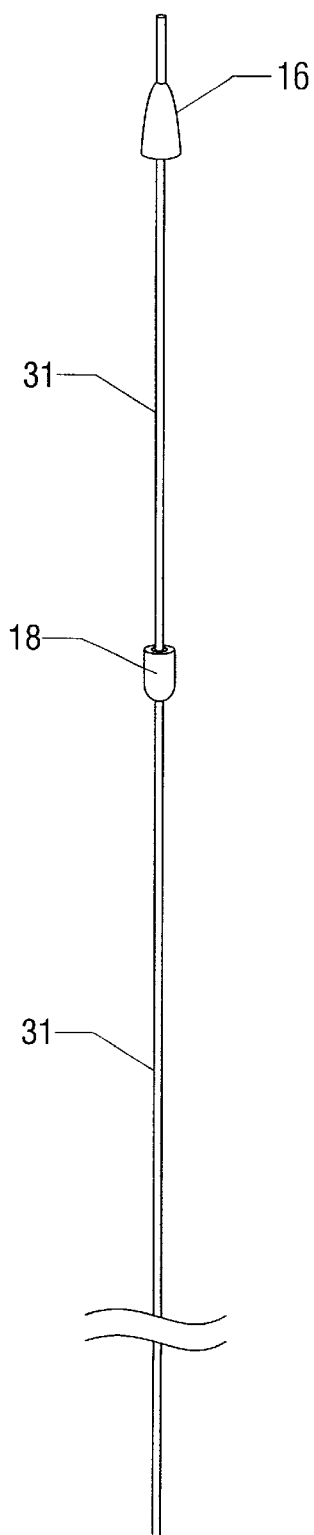
FIG. 11 is a perspective view of microtubing according to one embodiment of the present invention.

In another embodiment of the present invention shown in FIG. 11, microtubing 31 may be utilized instead of pusher wire 14. Advantageously, the microtubing may be rigid and flexible, thus providing stability as well as maneuverability to the system. Further, a guidewire (to be discussed below) may be utilized with microtubing 31. Blocking pieces 16 and 18 may be attached to microtubing 31 in the same manner in which they may be attached to pusher wire 14. As stated above, blocking piece 16 is optional. Microtubing 31 may be formed of any suitable material, such as nitinol.

In an embodiment useful for a single percutaneous insertion, microtubing 31 may have an outer diameter of 0.025 inches to 0.060 inches, and preferably 0.025 to 0.050 inches for use in vessels such as femoral arteries, and even more preferably 0.025 to 0.040 inches in such cases, and preferably 0.025 to 0.060 inches for use in vessels such as femoral veins, and even more preferably 0.025 to 0.040 inches in such cases, and preferably 0.025 to 0.050 inches for use in vessels such as carotid arteries, and even more preferably 0.025 to 0.040 inches in such cases. In such an embodiment, the inner diameter of microtubing 31 may be 0.018 inches to 0.054 inches, and preferably 0.018 to 0.038 inches for use in vessels such as femoral arteries, and even more preferably 0.018 to 0.032 in such cases, and is preferably 0.018 to 0.054 inches for use in vessels such as femoral veins, and even more preferably 0.018 to 0.038 inches in such cases, and is preferably 0.018 to 0.045 inches for use in vessels such as carotid arteries, and even more preferably 0.018 to 0.035 inches in such cases.

In an embodiment useful for surgical insertion, microtubing 31 may have an outer diameter of 0.025 inches to 0.080 inches, and preferably 0.025 to 0.060 inches for use for use in vessels such as femoral arteries, and even more preferably 0.025 to 0.040 inches in such cases, and preferably 0.025 to 0.080 inches for use in vessels such as femoral veins, and even more preferably 0.025 to 0.040 inches in such cases, and preferably 0.025 to 0.060 inches for use in vessels such as carotid arteries, and even more preferably 0.025 to 0.040 inches in such cases. In an embodiment useful for surgical insertion, microtubing 31 may have an inner diameter of 0.018 inches to 0.075 inches, and preferably 0.018 to 0.054 inches for use in vessels such as femoral arteries, and even more preferably 0.018 to 0.035 inches in such cases, and preferably 0.018 to 0.075 inches for use in vessels such as femoral veins, and even more preferably 0.018 to 0.035 inches in such cases, and preferably 0.018 to 0.054 inches for use in vessels such as carotid arteries, and even more preferably 0.018 to 0.035 inches in such cases. It is to be understood that the sizes above may differ according to the manner of insertion and the size of the vessel into which the delivery system is placed, as well as according to the size of catheter 20 of sheath 11, into which the microtubing is placed.

Figure 13:
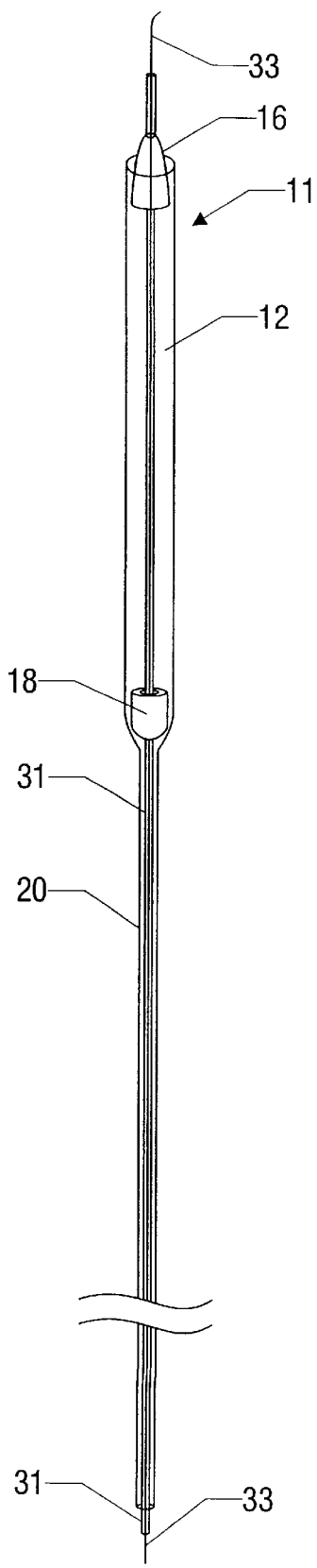
FIG. 13 is a perspective view of a portion of a double coaxial delivery system according to one embodiment of the present invention.

In another embodiment of the present invention shown in FIG. 13, guidewire 33 may be used with microtubing 31, such that the microtubing encloses the guidewire. Thus, the microtubing may be advanced and pulled back while enclosing the guidewire. In one embodiment, a guiding mechanism may be positioned in operative relation to the end of the microtubing. In one embodiment, a tip, such as tip 30, may be coupled to the end of the microtubing in order to serve as a guiding mechanism. In another embodiment, guidewire 33 may serve as a guiding mechanism.

In an embodiment in which guidewire 33 serves as a guiding mechanism, guidewire 33 should be appropriately sized to fit within the lumen of microtubing 31. For example, a guidewire with a diameter of 0.018 inches fits within a microtubing with an inner diameter of 0.020 inches. Thus, a difference of about 0.002 inches between the diameter of guidewire 33 and the inner diameter of microtubing 31 may be utilized to size the guidewire. In an embodiment useful for a percutaneous insertion, guidewire 33 may have a diameter of 0.018 inches to 0.052 inches, and preferably a diameter of 0.018 to 0.038 inches, and even more preferably a diameter of 0.018 to 0.032 inches. In an embodiment useful for surgical insertion, guidewire 33 may have a diameter of 0.018 inches to 0.052 inches, and preferably a diameter of 0.018 to 0.045 inches, and even more preferably a diameter of 0.018 to 0.035 inches. It is to be understood that the sizes above may differ according to the manner of insertion and the size of the vessel into which the delivery system is placed, as well as the size of the microtubing utilized.

Guidewire 33 may be formed of any suitable material, such as nitinol. It is to be understood that microtubing 31 may be utilized without guidewire 33. It is to be understood that in embodiments in which microtubing 31 is utilized without guidewire 33, another suitable guiding mechanism may be used. For instance, as discussed above, tip 14 may serve as a guiding mechanism and may be coupled to microtubing 31 for facilitating manipulation of the microtubing within the vessel.

In one embodiment of the present invention, using guidewire 33, the operator of the delivery system may advantageously have more freedom to negotiate tortuous vessels during delivery than when a guidewire is not utilized. A guidewire made from nitinol, for example, may also provide the operator with excellent torque-control thereby improving the maneuverability of the delivery system. Guidewire 33 or pusher wire 14 may be controlled by the operator with a wire control device 400, shown in FIG. 25 (pusher wire 14 is shown), such as the CRICKETT device (commercially available from Microvena), the FLOSWITCH HP device (commercially available from Boston Scientific), the PIN VISE device (commercially available from Cook), or the like.

As shown in FIG. 2A, catheter 20 and tapered connecting piece 22 fit inside the trailing portion of the delivery system 24, which may be a thin-walled sheath. As shown in FIG. 2A, the anchoring stent encloses catheter 20 and is enclosed by trailing sheath 24. In one embodiment, sheath 24 may be as large as, or slightly larger than sheath 11. In one embodiment, sheath 24 may also be slightly smaller than sheath 11.

In an embodiment useful for a single percutaneous insertion, the outer diameter of sheath 24 may be between 8-F and 14-F, and is preferably 9-F to 12-F for use in vessels such as femoral arteries, and even more preferably 10-F to 12-F in such cases, and is preferably 8-F to 14-F for use in vessels such as femoral veins, and even more preferably 10-F to 14-F in such cases, and is preferably 8-F to 12-F for use in vessels such as the carotid artery, and even more preferably 9-F to 10-F in such cases. In an embodiment useful for surgical insertion, the outer diameter of leading portion 12 may be between 8-F and 24-F, and is preferably 12-F to 16-F for use in vessels such as femoral arteries, and even more preferably 12-F to 14-F in such cases, and is preferably 12-F to 24-F for use in vessels such as femoral veins, and even more preferably 12-F to 16-F in such cases, and is preferably 8-F to 14-F for use in vessels such as the carotid artery, and even more preferably 10-F to 12-F in such cases. It is to be understood that the sizes above may differ according to the manner of insertion and the size of the vessel into which the delivery system is placed.

As shown in FIG. 2C, end 29 of trailing sheath 24 may overlap leading portion 12 of sheath 11 by 5 to 10 mm. In such an embodiment, end 29 may be slightly tapered and/or its wall thickness may be reduced such that the profile of the transition from sheath 11 to sheath 24 is smooth. The overlap also may serve to prevent the two sheaths from sliding apart during insertion and positioning of the delivery system. Further, the overlap may serve to reduce the amount of blood to which stage 1 (which may be enclosed by sheath 24 as discussed below) is exposed prior to the delivery of stage 1.

As shown in FIG. 2A, the anchoring stent 1 is held in place proximally by the widened leading portion of the delivery system and distally by a pusher catheter 26. Thus, in one embodiment, the proximal end of the anchoring stent may contact sheath 11, and the distal end of the anchoring stent may contact catheter 26. Pusher catheter 26 fits within the lumen of trailing sheath 24, and encloses catheter 20 of leading sheath 11. In one embodiment, end 25 of catheter 26 serves to release the anchoring stent from the delivery system during implantation by contacting the distal end of the anchoring stent as trailing sheath 24 is pulled back; thus, catheter 26 is in operative relation with sheath 24. Further, as the delivery system is being positioned within the vessel, catheter 26 may also serve to control the position of the anchoring stent within sheath 24 in a similar fashion. Catheter 26 may be formed from similar materials as those from which sheaths 11 and 24 may be formed.

The size of catheter 26 depends on many factors, including the sizes of catheter 20 and sheath 24. The outer diameter of catheter 26 may be about 2-F smaller than the size of catheter 24. In an embodiment useful for a single percutaneous insertion, the outer diameter of sheath 24 may be between 6-F and 12-F, and is preferably 7-F to 10-F for use in vessels such as femoral arteries, and even more preferably 8-F to 10-F in such cases, and is preferably 6-F to 12-F for use in vessels such as femoral veins, and even more preferably 8-F to 12-F in such cases, and is preferably 6-F to 10-F for use in vessels such as the carotid artery, and even more preferably 7-F to 8-F in such cases. In an embodiment useful for surgical insertion, the outer diameter of leading portion 12 may be between 6-F and 22-F, and is preferably 10-F to 14-F for use in vessels such as femoral arteries, and even more preferably 10-F to 12-F in such cases, and is preferably 10-F to 22-F when the delivery system is used in vessels such as femoral veins, and even more preferably 10-F to 14-F in such cases, and is preferably 6-F to 12-F for use in vessels such as the carotid artery, and even more preferably 8-F to 10-F in such cases. It is to be understood that the sizes above may differ according to the factors listed above, and according to the manner of insertion and the size of the vessel into which the delivery system may be placed.

As shown in FIG. 2D, in one embodiment of the present invention, blocking piece 23, similar to blocking piece 18, may be attached to portion 20 in the manner described above. Blocking piece 23 may serve the functions of catheter 26, and may therefore be used instead of catheter 26. Thus, the location of blocking piece 23 is such that blocking piece 23 is enclosed by or positioned within the sheath 24 during operation of the delivery system.

Figure 25:
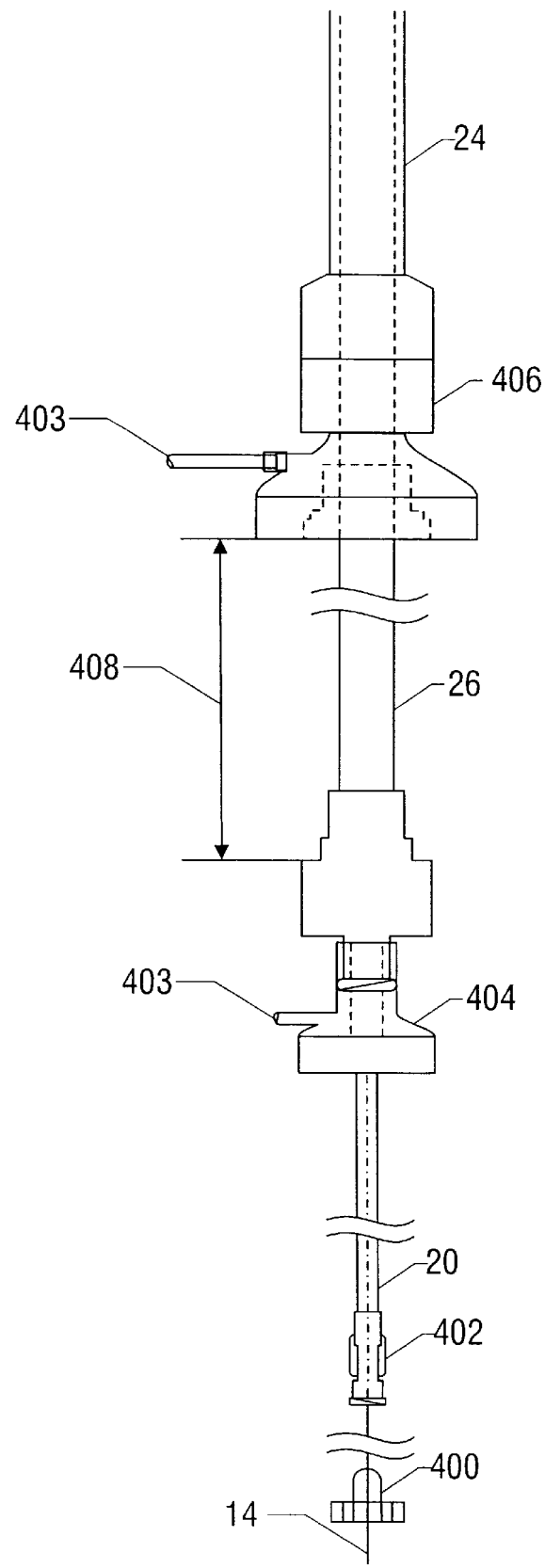
FIG. 25 is a front view of a double coaxial delivery system equipped with various control devices according to one embodiment of the present invention.

Turning to the control of the delivery system, in one embodiment of the present invention, the delivery system may be controlled using the following well-known control devices, shown in FIG. 25. The position of microtubing 31 (not shown) with respect to guidewire 33 may be controlled using a standard attachment well known in the art, such as the FLOSWITCH HP device (commercially available from Boston Scientific).

Figure 6A:
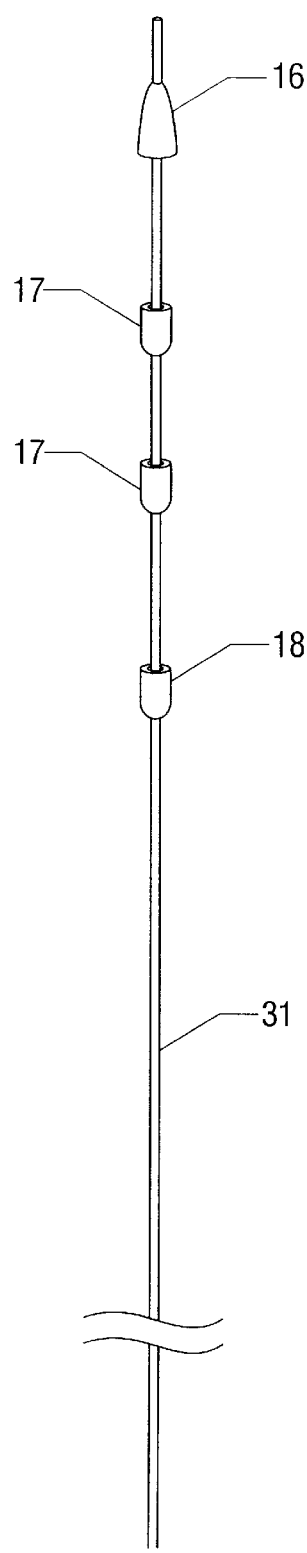
FIG. 6A is a perspective view of microtubing with adjustable plungers according to one embodiment of the present invention.
Figure 6B:
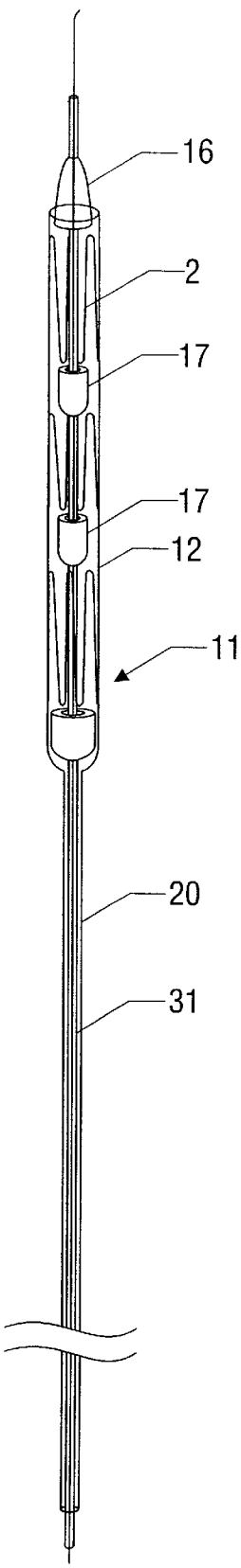
FIG. 6B is a perspective view of a partially assembled delivery system according to one embodiment of the present invention.
Figure 16:
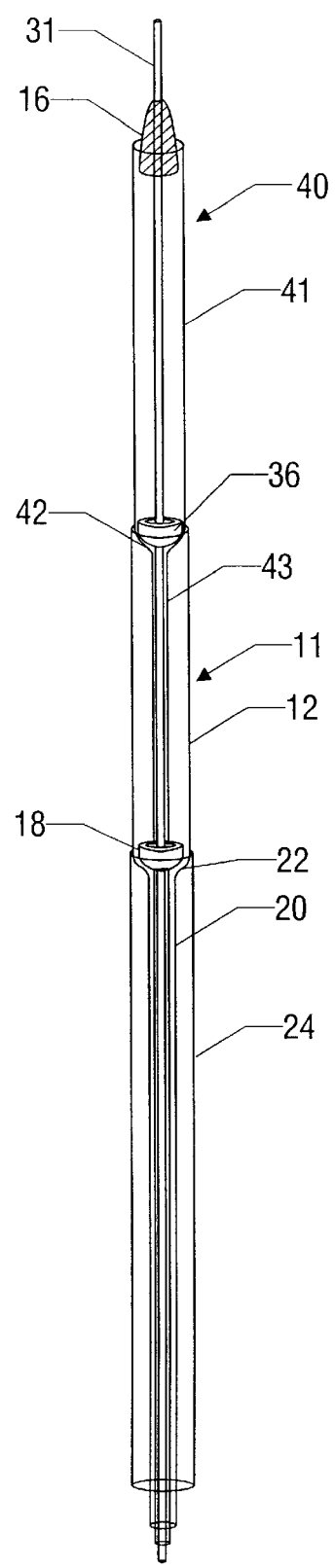
FIG. 16 is a perspective view of a triple coaxial delivery system according to one embodiment of the present invention.

The position of sheath 11 (which is configured to fit over and enclose pusher wire 14 as shown in FIG. 2A, or microtubing 31 as shown in FIG. 6B) with respect to either pusher wire 14 or microtubing 31 may be controlled as follows. A female hub 402, such as a Luer female hub (commercially available from Cook), may be attached to the end of catheter 20 of sheath 11. A male connector, such as a Luer stopcock (not shown) (also commercially available from Cook), through which the wire or microtubing is threaded, may engage the female hub, thereby securing the position of sheath 11 with respect to the wire or the microtubing. Further, the male connector may be provided with a side arm for hemostasis. Saline may also be injected through the side arm and into sheath 11 in order to prevent thrombi from accumulating within the lumen of sheath 11. Contrast material may also be injected through the side arm and into sheath 11 in order to better identify the position of the delivery system under fluoroscopy. In this regard, as shown in FIG. 16, in one embodiment of the present invention, sheath 11 (and sheath 40 to be discussed below) may be provided with one or more fluid openings 51 defined in at least catheter 20, through which contrast material may flow in order to be distributed to the areas surrounding the openings. This may be advantageous in the situation in which, for example, sheath 24 has been withdrawn so as to deliver stage 1, and contrast material may no longer be delivered to the area which was enclosed by sheath 24. Two such male connectors that may be provided with side arms 403 are the CHECK FLO adapter 404 (shown in FIG. 25 as connected to catheter 26) (commercially available from Cook), and the TOUHY-BORST adapter (also commercially available from Cook).

Figure 26:
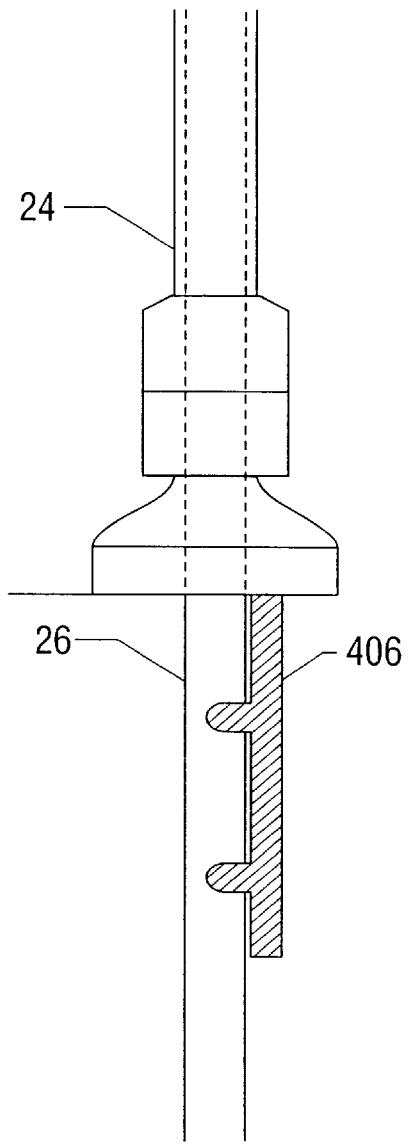
FIG. 26 is a front view of a portion of a double coaxial delivery system equipped with a removable sliding blocker according to one embodiment of the present invention.
Figure 27:
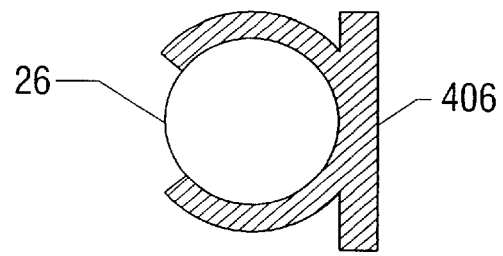
FIG. 27 is a cross-sectional view of the removable sliding blocker shown in FIG. 26.

The position of catheter 26 with respect to portion 20 of sheath 11 may be controlled with the same devices for controlling sheath 11. In one embodiment of the present invention, the position of catheter 26 may be fixed relative to the position of catheter 20. The position of sheath 24 with respect to catheter 26 may also be controlled using these same devices. In one embodiment, instead of attaching a female hub to sheath 24, sheath 24 may be equipped with an adapter 406, such as a CHECK FLO adapter, without a separate female hub, as is well-known in the art. In another embodiment, a slide-proof connection may be achieved between sheath 24 and catheter 26 by providing removable sliding blocker 406, shown in FIGS. 26 and 27. This blocker may be appropriately labeled (such as "Safety Lock") and may be removed just prior to delivery of stage 1 (to be discussed below).

In one embodiment of the present invention, at the end of the delivery system nearest the operator, the distances between the control devices are selected so as to allow the stages to be delivered without the control devices running into each other. For example, distance 408 may be chosen such that sheath 24 may be pulled back far enough to allow stage 1 to be released without the control devices attached to sheath 24 and catheter 26 interfering with each other.

As shown in FIG. 2A, stages 1 and 2 are loaded within a delivery system, according to one embodiment of the present invention. To assemble the delivery system as shown in FIG. 2A, small caliber catheter 20 may be positioned in the lumen of stage 1 of the graft. Stage 1 may then be compressed around catheter 20 such that the two form a unit. In one embodiment of the present invention in which blocking piece 23 is utilized, stage 1 may be positioned between leading portion 12 and blocking piece 23, and then stage 1 may be compressed around catheter 20 to form a unit.

Sheath 24 may then be positioned or pulled over the unit so as to enclose the unit and hold it in place. It is to be understood that in another embodiment, stage 1 also may be compressed and placed within sheath 24 before catheter 20 is placed within stage 1, whether or not blocking piece 23 is utilized.

Using a front-loading technique, pusher wire 14 may be placed into the leading portion 12 of sheath 11, such that the blocking pieces are still outside leading portion 12. It is to be understood that microtubing 31 (not shown) may be used instead of pusher wire 14. The inner or scaffolding stent 2 may be placed over pusher wire 14 so as to enclose pusher wire 14, and stage 2 may be positioned between the blocking pieces 16 and 18. It is to be understood that stage 2 may be placed over the wire before the wire is placed within sheath 11. The inner or scaffolding stent may then be compressed around the wire, and leading portion 12 of sheath 11 may be positioned over the compressed scaffolding stent so as to enclose it and hold it in place. It is to be understood that stage 2 may also be compressed and positioned within leading portion 12, and pusher wire 14 may then be placed within stage 2. Pusher wire 14 may be positioned within sheath 11 such that blocking piece 18 rests against the tapered portion connecting leading portion 12 and catheter 20.

Catheter 26 may then be placed coaxially over small caliber catheter 20 into the lumen of the outer thin-walled sheath 24 and may be used as a pusher/holding catheter for stage 1 of the graft. It is to be understood that catheter 26 may be placed over small caliber catheter 20 before or after stage 2 is enclosed by sheath 11.

It also is to be understood that stage 1 may be positioned within sheath 24 before or after stage 2 is positioned within sheath 11.

It is to be understood that any suitable stents may be loaded into the double coaxial delivery system of the present invention. For example, in one embodiment of the present invention, an anchoring stent that is similar to the one shown in FIG. 1A, but to which a graft material is coupled using the non-overlap method described above, may be utilized. By coupling the cover material to the anchoring stent, at least a portion of one of the two radially compressible spring stents may contact a vessel upon delivery of the outer stage into the vessel. Like the anchoring stent shown in FIG. 1A, such an anchoring stent may be compressed around portion 20 of sheath 11 and sheath 24 may be placed around it so as to enclose it. In another embodiment of the present invention, the anchoring stent shown in FIG. 4 to which a graft material is coupled using the non-overlap method may also be utilized in the same fashion. In yet another embodiment of the present invention, as discussed above, self-expanding tube stents may be utilized for either stage 1 or stage 2.

In one embodiment of the present invention shown in FIGS. 5A and SB, during deployment or delivery of a two stage stent (to be discussed in greater detail below), if only the distal most portion of the scaffolding stent (denoted by arrows 250) is supported by blocking piece 18, the separate serpentine stents might be crammed into each other within the delivery sheath because the serpentine stents are supported by only one connecting bar between each spring stent. To avoid that result, as shown in FIGS. 6A and 6B, adjustable plungers 17, which may have circular indentations as discussed above, may be attached to microtubing 31 (or pusher wire 14 not shown) in a manner similar to that described above with respect to the adjustable plungers that may be used for blocking piece 18. Plungers 17 may be positioned in spaced relation to each other so as to evenly transmit the longitudinal delivery force applied to scaffolding stent 2 during delivery thereof to each serpentine stent or body of stage 2. In another embodiment of the present invention, the longitudinal delivery force may be evenly transmitted to each serpentine stent of the scaffolding stent by attaching firm connections (not shown) between the bodies of the scaffolding stent such as reinforcement wires (not made from the same single wire as the scaffolding stent) at appropriate locations (such as on the opposite side of the scaffolding stent from the connecting bars 8). These reinforcement wires may be attached to the bodies by any suitable means such as welding, by crimping metal clips on the wires, and the like.

In one embodiment of the present invention, once the delivery system has been loaded with the stages and assembled, the devices for controlling the delivery system may be placed in the positions above described.

For insertion and deployment of a multi-stage stent graft, the loaded delivery system may be inserted into a blood vessel in a single percutaneous insertion or through a surgical insertion. Referring to FIG. 2A, stage 2, the inner stage enclosed by sheath 11, is positioned in front of stage 1, the outer stage enclosed by sheath 24, such that stage 2 is inserted into the vessel before stage 1 is inserted into the vessel, just as sheath 11 is inserted into the vessel before sheath 24. The position of the stages within the device may be monitored using fluoroscopy, and further by injecting contrast material into the various sheaths and the microtubing as above described. Stage 1, enclosed by sheath 24, is positioned within the vessel. In an embodiment in which guidewire 33 is used, this positioning may be accomplished by inserting the guidewire into the vessel first, and then sliding the rest of the delivery system along the guidewire to the appropriate position. In an embodiment in which pusher wire 14 is used, or microtubing 31 is used without the guidewire, this positioning may occur by guiding the system to the appropriate position. After guiding the device to the desired position, the successive layers or stages of the graft are released with the outermost layer being released first. To accomplish the release, the trailing sheath 24 (the portion of the delivery system surrounding or enclosing the outer stage) is pulled back while holding in place the pusher/catheter 26. The portion of the delivery system immediately in front of the trailing portion is then pulled back into the outer stage. Then the inner stage is released into the outer stage by pulling back sheath 11, which surrounds the inner stage, so as to endovascularly assemble the stent graft. As will be appreciated by those skilled in the art, by using successive stages and coaxial delivery systems, multi-stage stent grafts containing the desired number of layers or stages can be delivered and assembled endovascularly.

As stated above, prior to inserting the delivery system into a vessel an introducer sheath may be utilized. In one embodiment, this introducer sheath may be equipped with a check flow adapter and side arm fitting. In one embodiment in which a single percutaneous insertion is made in the femoral artery, the introducer sheath may be placed into the artery after a percutaneous puncture is made. The femoral introducer sheath may then remain in the femoral artery as the delivery system is inserted into it and positioned. The size of the femoral sheath will depend on the size of sheaths 11 and 24. If a femoral introducer sheath is used for access via a femoral artery, the outer diameter of the introducer sheath may be 12-F, or smaller. The use of a femoral introducer sheath is optional, as with all catheter-related interventions, and, if used, may be withdrawn after the delivery system has been inserted into the vessel to avoid interfering with the operation of sheath 24. Introducer sheaths may also be used when insertions are made in vessels such as the carotid artery, or in the femoral vein. For the latter, an outer diameter of 14-F is acceptable. Introducer sheaths are not needed for surgical insertions.

To further illustrate this embodiment, the delivery and assembly of a two stage stent system of FIG. 1A and FIG. 1B by the delivery system of FIG. 2A is described. The delivery system is positioned in the aorta via the optional femoral sheath so that the mid-portion containing the covered graft stage 1 is infrarenal and the leading portion 12 of the delivery system containing the inner scaffolding stent 2 is located more cephalad in the aorta. Thus, the inner stage is located cephalad of the outer stage, or closer to the head of the patient than is the outer stage. Once stage 1 is in the appropriate position, the pusher/holding catheter 26 is held stationary and the outer sheath 24 is pulled back releasing stage 1 into the vessel, such that stage 1 engages the vessel. The outer sheath 24 containing the pusher/holding catheter 26 is then withdrawn into the femoral sheath so that it does not interfere with the last phase of graft deployment. If blocking piece 23 is utilized instead of holding catheter 26 as described above, blocking piece 23 is held stationary by so holding pusher wire 14 or sheath 11 to which the blocking piece may be attached. Stage 1 may then be delivered by pulling back sheath 24 as just described.

Figure 3:
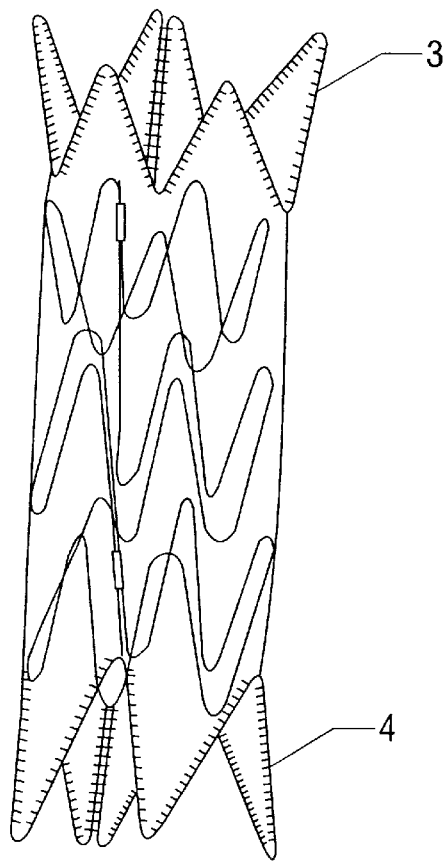
FIG. 3 is a perspective view of a two stage stent graft after assembly according to one embodiment of the present invention.

In the second step of the delivery, sheath 11 is withdrawn until the inner stage 2 is positioned within the lumen of the polyester graft tube 6 between the two serpentine stents 3 and 4. In another embodiment, the inner stage may be chosen so as to overlap the serpentine stents of the outer stage. Once the inner scaffolding stent 2 is in place, the pusher wire 14, or microtubing 31 depending on which is being used, is held stationary and the inner scaffolding stent 2 is released from within the front portion 12 and into stage 1 by pulling the small caliber catheter 20 back. The endovascularly assembled aortic graft is illustrated in FIG. 3, the scaffolding stent 2 is positioned within graft material 6 of the anchoring stent 1.

Figure 14:
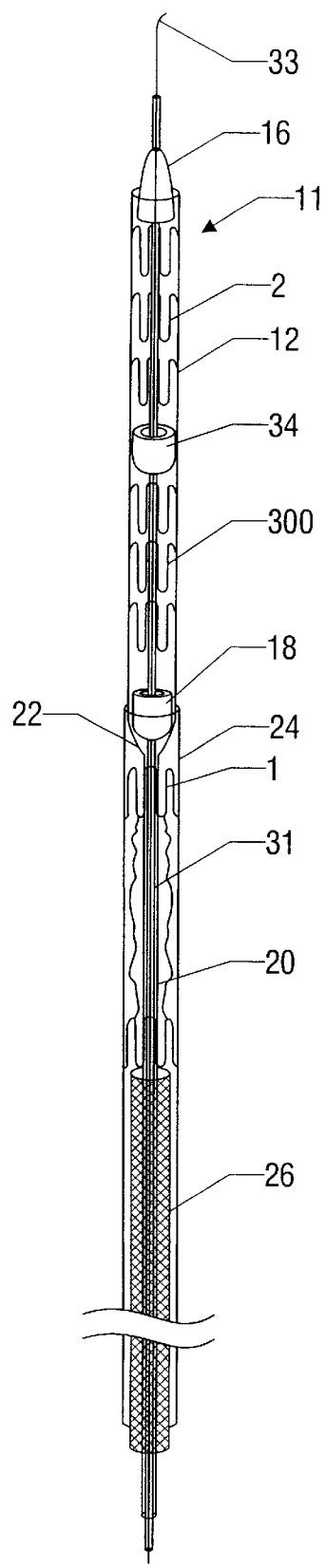
FIG. 14 is a perspective view of a double coaxial delivery system loaded with three stages according to one embodiment of the present invention.

In another embodiment of the present invention, a three-stage stent graft may be delivered utilizing the coaxial delivery system just described. In a first version in which a three-stage stent graft may be so delivered shown in FIG. 14, the stages may be loaded into the delivery system as the delivery system is assembled in a very similar manner to that above described. Stage 1 may be loaded as above described. Then, the third stage, denoted as 300, may be loaded next, followed by the loading of stage 2. Both the third stage and stage 2 may be loaded in a manner similar to that described above for loading stage 2. The difference being that blocking piece 34 may be placed on microtubing 31 (or pusher wire 14, not shown) between blocking pieces 16 and 18 in order to separate stage 2 from the third stage. Blocking piece 34 may have a circular indention on one or both surfaces for the reasons above described. During delivery, blocking piece 34, may serve to "push" stage 2 as the delivery system is advanced and it may also serve to "pull" the third stage when the delivery system is withdrawn. Further, when stage 2 is delivered or released into stage 1, blocking piece 34 may serve to support the distal end of stage 2 as sheath 11 is pulled back. Thus, as shown in FIG. 14, the three stages are positioned such that stage 2, the intermediate stage, is inserted into the vessel first; the third stage, the inner stage, is inserted into the vessel second; and stage 1, the outer stage, is inserted into the vessel last.

In the first version, after the stages have been loaded into the delivery system and the delivery system has been assembled, the three-stage stent graft may be inserted into a vessel and endovascularly assembled as follows. The stages may be inserted into the vessel in the order above described, in a single percutaneous insertion. Stage 1 may be positioned and released into the vessel, thereby engaging the vessel, in the manner above described. Stage 2 may then be positioned within stage 1. Stage 2 may then be released into stage 1, thereby engaging stage 1, in the manner above described. Leading portion 12 should remain positioned around and enclosing stage 3 subsequent to the release of stage 2.

Next, sheath 11 and microtubing 31 (or pusher wire 14, not shown) may be advanced proximally over guidewire 33 (a cephalad movement—towards the head—when, for example, an abdominal aortic aneurysm is being stent grafted) while holding the guidewire stationary until the third stage (denoted as 300) is positioned within the lumen of stage 2. The third stage may then be released into stage 2, thereby engaging stage 2, by holding microtubing 31 stationary and withdrawing or pulling back the small caliber catheter 20 of sheath 11. It is to be understood that if the third stage is longer than stage 2, it may overlap stage 2 and also engage a portion of stage 1.

Figure 15:
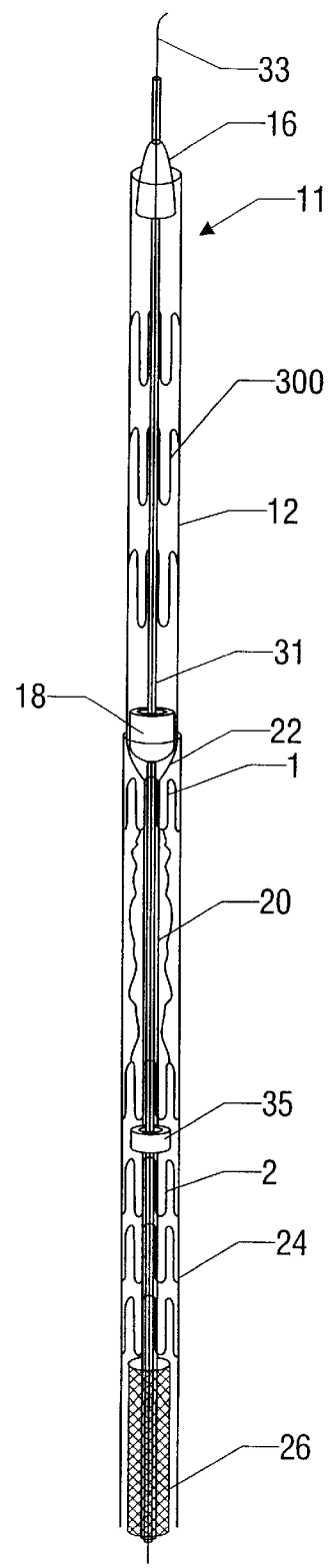
FIG. 15 is a perspective view of another double coaxial delivery system loaded with three stages according to one embodiment of the present invention.

In a second version in which a three-stage stent graft may be delivered utilizing the coaxial delivery system as shown in FIG. 15, stage 1 may be loaded within trailing portion 24 as above described. Stage 2 may be loaded so as to be positioned distally behind stage 1. Thus, stage 2 may be positioned between an intermediate blocking piece 35 and catheter 26. Instead of catheter 26, a blocking piece may be attached to catheter 20 (or pusher wire 14, not shown) as above described. Blocking piece 35, like blocking piece 34, may have circular indentions on either or both surfaces and serves the same function with respect to stages 1 and 2 as intermediate blocking piece 34 serves with respect to stage 2 and the third stage as above described. As shown in FIG. 15, the third stage (denoted as 300) may be loaded so as to be positioned within leading portion 12 of sheath 11. Thus, as shown in FIG. 15, the three stages are positioned such when inserted into a vessel, the third stage, the inner stage, is inserted into the vessel first; stage 1, the outer stage, is inserted into the vessel next; and stage 2, the intermediate stent, is the last of the three stages to be inserted into the vessel.

As shown in FIG. 15, blocking piece 35 is positioned between catheter 26 (or the blocking piece (not shown) that may be used instead of catheter 26) and the proximal end of sheath 24.

In the second version, after the stages have been loaded into the delivery system as described above, the three-stage stent graft may be inserted into a vessel and endovascularly assembled as follows. The stages may be inserted into the vessel in the order above described, in a single percutaneous insertion. Stage 1 may be positioned and released into the vessel, thereby engaging the vessel, in the manner above described. Sheath 24 should remain positioned around and enclosing stage 2 subsequent to the release of stage 1. Then, the delivery system may be advanced proximally (a cephalad movement in the case of an abdominal aortic aneurysm) over the guidewire, which may be held stationary, until stage 2 is positioned within the lumen of stage 1. Once stage 2 is properly positioned, stage 2 may be released into stage 1, thereby engaging stage 1, in the manner in which stage 1 was released. Then, sheath 11 and microtubing 31 (or pusher wire 14, not shown) may be withdrawn distally over guidewire 33, which may be held stationary, until the third stage (denoted 300) is positioned within the lumen of stage 2. Once stage 3 is properly positioned, stage 3 may be released into stage 2, thereby engaging stage 2, in the manner in which stage 2 and the third stage were released in version 1. As with version 1, it is to be understood that if the third stage is longer than stage 2, it may overlap stage 2 and also engage a portion of stage 1.

Figure 17:
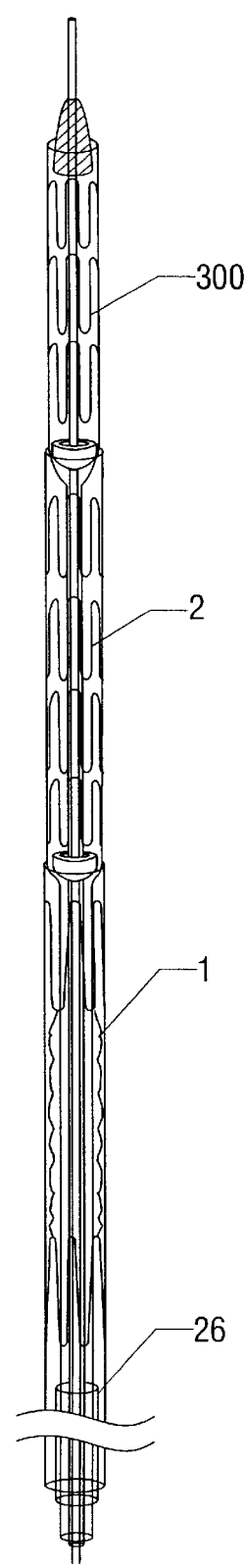
FIG. 17 is a perspective view of a triple coaxial delivery system loaded with three stages according to one embodiment of the present invention.
Figure 18:
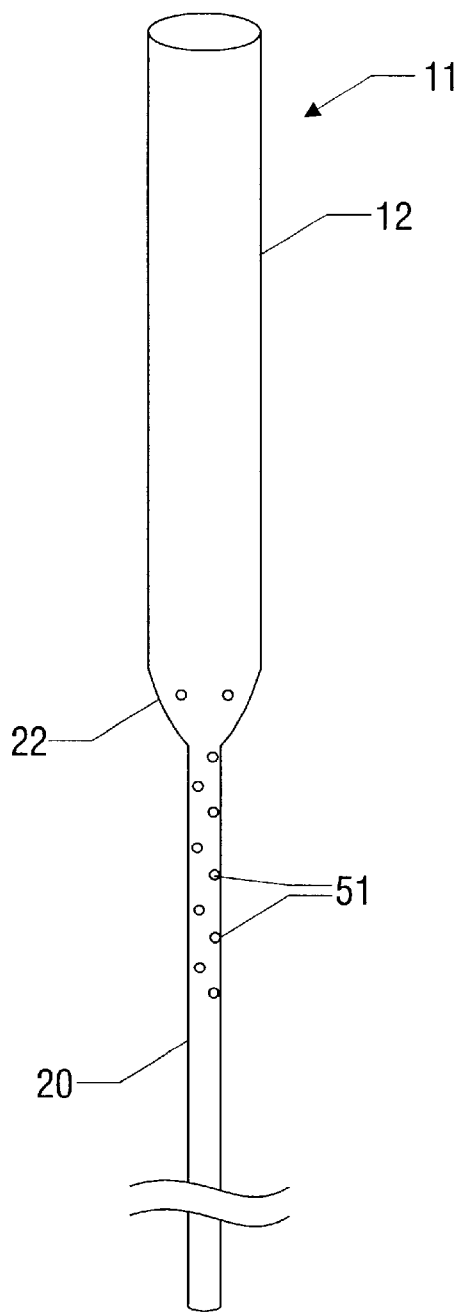
FIG. 18 is a perspective view of a sheath having one or more fluid openings defined therein according to one embodiment of the present invention.

In yet another embodiment of the present invention, a three-stage stent graft may be delivered and endovascularly assembled utilizing the triple coaxial delivery system shown in FIGS. 16 and 17. This delivery system operates in a similar fashion to the delivery system described above, and is equipped with a third sheath 40 which is similar in form and function to sheath 11. As shown in FIG. 16, sheath 40 has a first portion 41 having a caliber of about 10-F to 12-F, including 10.5-F, 11-F, and 11.5-F, and a second portion 43 having a caliber of about 2-F to 3-F, including 2.5-F. Portions 41 and 43 are connected by tapered portion 42. In one embodiment of the triple coaxial delivery system, sheath 11 may overlap sheath 40 as above described. As with sheath 11, sheath 40 may be formed of one contiguous sheath. In another embodiment, sheath 40 may be formed of two separate sheaths 41 and 43, and connecting piece 42 that may be separate from both sheaths or formed contiguously with either. Although not shown, it is to be understood that connecting piece 42 (as well as connecting piece 22) may be formed so as not to be tapered. The size of catheter 20 of sheath 11 may be increased slightly to ensure that portion 43 can fit within and be enclosed by it. Additionally, the inner diameter of blocking piece 18 may be adjusted so as to allow it to fit around portion 43 instead of microtubing 31. Also shown in FIG. 16 is blocking piece 36, which is similar in form and function to blocking piece 18. Blocking piece 36 may be attached to the microtubing (which may enclose guidewire 33, not shown) or pusher wire 14 (not shown) as described above with respect to blocking piece 18.

FIG. 17 shows the triple coaxial delivery system assembled and loaded with the three stages of the stent graft. Stages 1 and 2 may be loaded in the manner described above regarding a two-stage stent, and the third stage (denoted as 300) may be loaded like stage 2. Thus, as shown in FIG. 17, the three stages are positioned within the triple coaxial delivery system such that the third stage, the inner stage, may be inserted into a vessel first; stage 2, the intermediate stage, may be inserted into the vessel after the third stage; and stage 1, the outer stage, is inserted into the vessel after stage 2.

Control of the triple coaxial delivery system may be achieved using the devices above described.

After the stages have been loaded into the triple coaxial delivery system as just described, the three-stage stent graft may be inserted into a vessel and endovascularly assembled as follows. The stages may be inserted into the vessel in the order above described, in a single percutaneous insertion. Stage 1 may be positioned and released into the vessel, thereby engaging the vessel, in the manner above described. Stage 2 also may be positioned and released into stage 1, thereby engaging stage 1, as above described with regard to delivery of a two-stage stent graft. The only difference being that instead of holding microtubing 31 stationary while withdrawing sheath 11, portion 43 of sheath 40 may be held stationary while sheath 11 is withdrawn. Then, the third stage may be positioned within the lumen of stage 2 and then released into stage 2, thereby engaging stage 2, in a manner similar to the release of stage 2, that is, by holding the microtubing stationary and withdrawing sheath 40. It is to be understood that if the third stage is longer than stage 2, it may overlap stage 2 and also engage a portion of stage 1.

For any of the above embodiments involving the delivery of three stages, any suitable stent may be used for the third stage, as was the case with stages 1 and 2.

The delivery systems of the present invention described herein may be useful in the treatment of abdominal aortic aneurysms. As discussed, in such cases, a multi-stage stent graft may be loaded into a delivery system which may then be inserted into a femoral artery, thus taking a femoral approach. It is to be understood that the delivery systems of the present invention described herein may also be useful for endovascularly assembling multi-stage stent grafts in the following vessels, using the following approaches: in the treatment of thoracic aortic aneurysms ("TAA") using a femoral, or carotid approach; in the treatment of damaged iliac arteries using a carotid, subclavian, or brachial approach; and in the treatment of venous stenoses on larger veins such as the inferior vena cava ("IVC") using a femoral vein approach, or the superior vena cava ("SVC") using a femoral vein approach. It is also to be understood that the delivery systems of the present invention described herein may be useful in stent-grafting any tubular structure capable of receiving a covered or multi-layer stent graft, such as a biliary system stenosed by a tumorous lesion using a percutaneous insertion on the biliary tree or endoscopic approach through the mouth; a ureter stenosed or obstructed by a tumorous lesion using a percutaneous antegrade nephrostomy; or a tracheo-bronchial system such as a main bronchi stenosed by a tumorous lesion using a tracheal tubing as an approach. It is also to be understood that the delivery systems of the present invention described herein may be useful in creating transjugular intrahepatic portosystemic shunts ("TIPS") to decrease portal hypertension using a percutaneous internal jugular vein approach, or in repairing colonic strictures caused by malignant tumors using an endoscopic approach, and the like.

The sizes of sheaths 11 (both portions, 12 and 20) and 24, and the size of catheter 26 would be similar to the sizes listed above for treating a TAA from a carotid or subclavian approach using surgery or percutaneous entry. For treating the iliac arteries via a carotid, subclavian, or brachial approach via surgical or percutaneous entry, such sizes would be proportionately reduced from those listed above such that entry diameter would preferably be 10-F or smaller. For treating the IVC from a femoral vein using either insertion, such sizes would be similar to those listed above for the aortic system. For treating a biliary system via percutaneous entry, up to a 12-F outer diameter system may be used. For treating a main bronchi via a tracheal tubing, an even larger system than that described above may be used. For treating a TIPS via a right internal jugular vein, up to a 14-F outer diameter system may be used. For a colon via endoscopy, a system with an outer diameter of 10-F may be used.

The following example is included to demonstrate specific embodiments of the invention. It should be appreciated by those of skill in the art that the techniques disclosed in the example which follows represent techniques discovered by the inventors to function well in the practice of the invention, and thus can be considered to constitute specific embodiments for its practice. However, those of skill in the art should, in light of the present disclosure, appreciate that many changes can be made in the specific embodiments which are disclosed and still obtain a like or similar result without departing from the spirit and scope of the invention.

EXAMPLE 1

MATERIALS AND METHODS

Graft Construction

Figure 20:
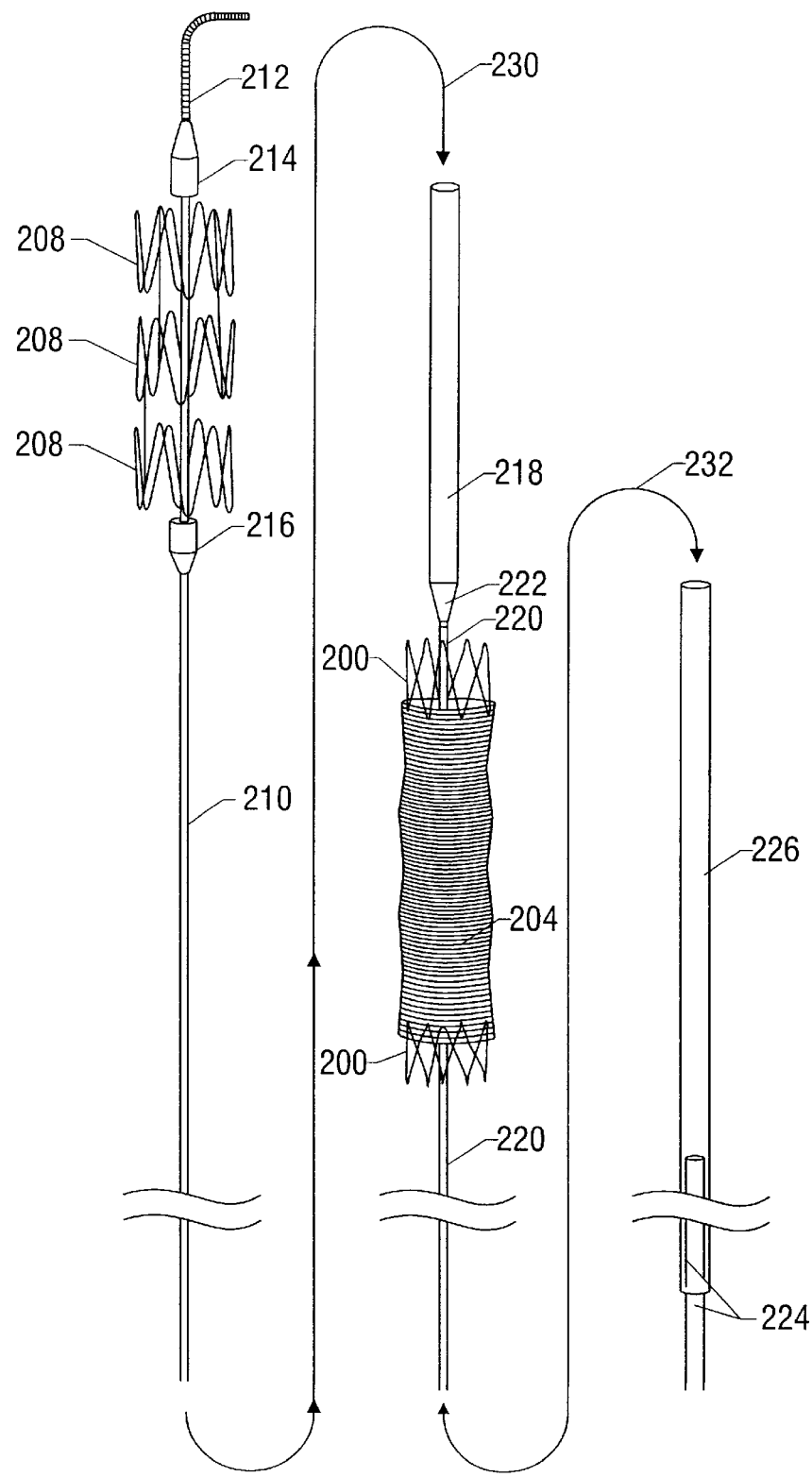
FIG. 20 depicts the loading of stages into and assembly of a double coaxial delivery system according to one embodiment of the present invention.

An aortic stent graft was made that consisted of two separate stages. As shown in FIG. 20, the first stage, the anchoring stent, consisted of two five-bend anchoring Z-stents 200 made of 0.012-inch stainless steel wire each with an unconstrained diameter of 14–16 mm. The stents were connected by two stainless steel wire (0.010-inch) struts (not shown)creating a unit 78–82 mm long. Eyes were formed at the inner bends of each stent by placing a bead of solder just above the bend. A tube 204 of polyester fabric 10 mm in diameter was formed by heat-sealing the edges. The fabric (PeCap® polyester; Tetko Inc., Briarcliff Manor, N.Y.) had a thickness of 61 $\mu$m and pore size of 95 $\mu$m. The tube was attached to the eyes of the anchoring stents with polypropylene suture (Prolene-5; Ethicon Inc., Sommerville, N.J.) so that one-third of each Z-stent was covered by the fabric.

The second stage of the stent graft was a triple-body inner scaffolding stent composed of three six-bend Z-stents 208 constructed from 0.010-inch stainless steel wire. Each stent was 14 mm in length and 13–14 mm in unconstrained diameter. The stents were connected to each other with two stainless steel wire (0.010-inch) struts. Neither the anchoring stent nor the scaffolding stent contained barbs.

Delivery System

As shown in FIG. 20, a delivery system composed of two independent coaxial delivery mechanisms was constructed for the two-stage deployment of the graft. One delivery mechanism consisted of a 0.014-inch stainless steel pusher wire 210. The front part of the wire was equipped with a 5-cm long piece of 0.028-inch flexible stainless steel guide wire 212 that had an angled tip and a tapered piece of a dilator 214 to facilitate manipulation within the vasculature. The section of the pusher wire that was located just behind the inner scaffolding stent was widened, forming a blocking piece 216, so that the wire would be suitable for pushing or stabilizing the stent. The remainder of the delivery mechanism was constructed of a 10-F OD thin-walled Teflon sheath 218 connected to a 4-F Teflon catheter 220 by using a tapered Teflon connecting piece 222. The connecting piece and the 4-F Teflon catheter were flared together and then the pieces were joined with a Silastic medical adhesive (Dow Corning, Midland, Minn.).

The other delivery mechanism consisted of a 9-F Teflon catheter 224 placed coaxially over the 4-F Teflon catheter, and a 12-F OD Teflon sheath 226 pulled over catheter 224. The 9-F Teflon catheter was used as a pusher/holding catheter for the first stage of the graft.

Assembly of the Delivery System

Figure 21:
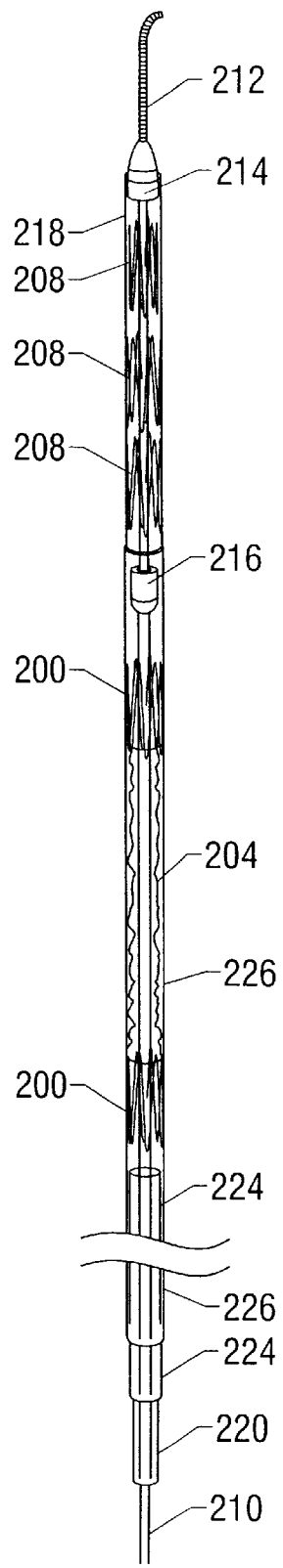
FIG. 21 is a perspective view of a double coaxial delivery system loaded with two stages according to one embodiment of the present invention.

First, using a front-loading technique, the 0.014-inch stainless steel pusher wire 210 was placed into the 10-F OD Teflon sheath 218 attached to the 4-F catheter 220, as indicated by arrow 230 in FIG. 20. The inner scaffolding stent was placed over the wire and positioned between the tapered dilator 214 and the blocking piece 216. The scaffolding stent was then compressed around the pusher wire and placed into the 10-F OD Teflon sheath 218. The proximal end of the tapered segment of dilator 214 fit into the distal end of the 10-F OD sheath 218, as shown in FIG. 21. The catheter 220 was positioned in the lumen of the outer covered portion of the graft which was then compressed around the catheter. The 12-F OD Teflon sheath 226 was pulled over the covered portion of the graft to hold it in place, as indicated by arrow 232. The 9-F Teflon catheter 224 stabilized the covered portion of the graft within the lumen of the 12-F OD sheath. FIG. 21 shows the parts of the grafts in relation to each other after assembling the delivery system.

Animal Evaluation

All experimentation involving animals was approved by the Institutional Animal Care and Use Committee of our institution. Animals were maintained in facilities approved by the Association for Assessment and Accreditation of Laboratory Animal Care (AAALAC International) and in accordance with current U.S. Department of Agriculture, Department of Health and Human Services, and National Institutes of Health regulations and standards.

Four adult mongrel dogs (22.5–31.2 kg) were used to test deployment of the graft using the double coaxial delivery system. Each dog was anesthetized by intravenous injection of pentothal (18.25 mg/kg), and then placed on inhalation anesthesia consisting of halothane (1.5%), nitrous oxide (0.3 L/min), and oxygen (0.8 L/min). The right carotid and right femoral arteries were surgically isolated and a 6-F and a 12-F introducer sheath was inserted into the respective vessels. Sodium heparin (100 units/kg) was given intravenously. Biplane abdominal aortography was performed through a 6-F catheter placed via the carotid approach.

Figure 22:
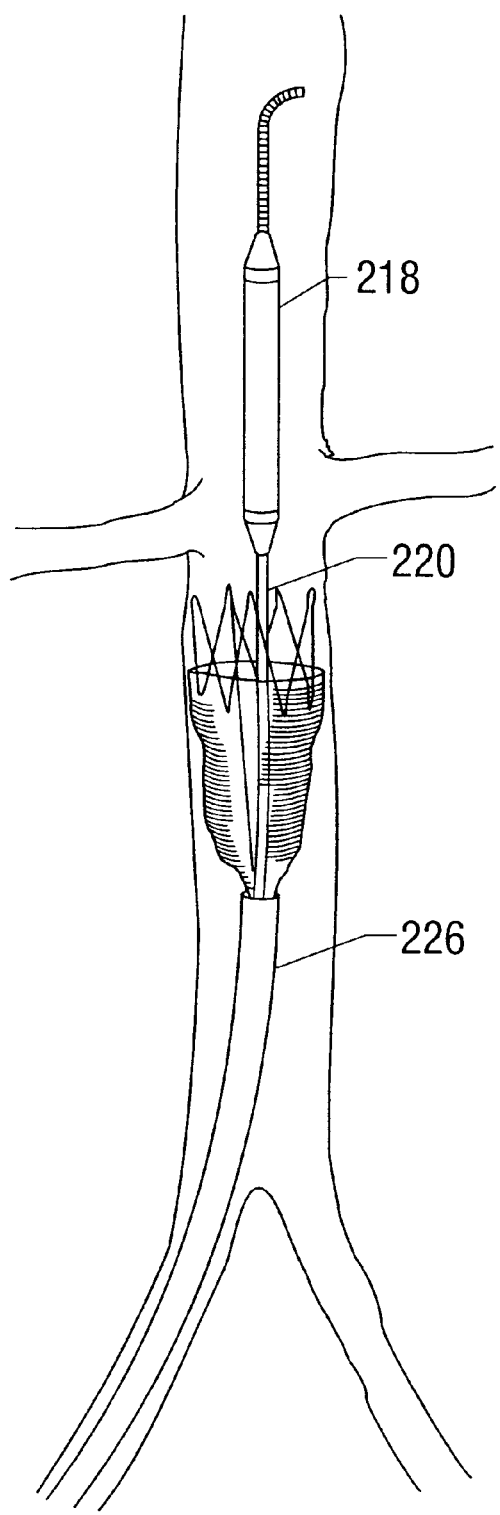
FIG. 22 is a perspective view depicting the release of stage 1 into a vessel using a double coaxial delivery system according to one embodiment of the present invention.

As shown in FIG. 22, the delivery system was introduced through the right femoral artery and positioned in the aorta so that the portion containing the first stage was infrarenal and the leading portion of the delivery system containing the inner scaffolding stent was located more cephalad in the aorta. The front Z-stent of the anchoring stent was used to guide graft placement within the aorta. Once the covered portion of the graft was in the appropriate position, the 9-F pusher/holding catheter (not shown) was held stationary and the 12-F OD Teflon sheath 226 was pulled back releasing the covered unit. The 12-F OD sheath containing the pusher/holding catheter was then removed.

Figure 23:
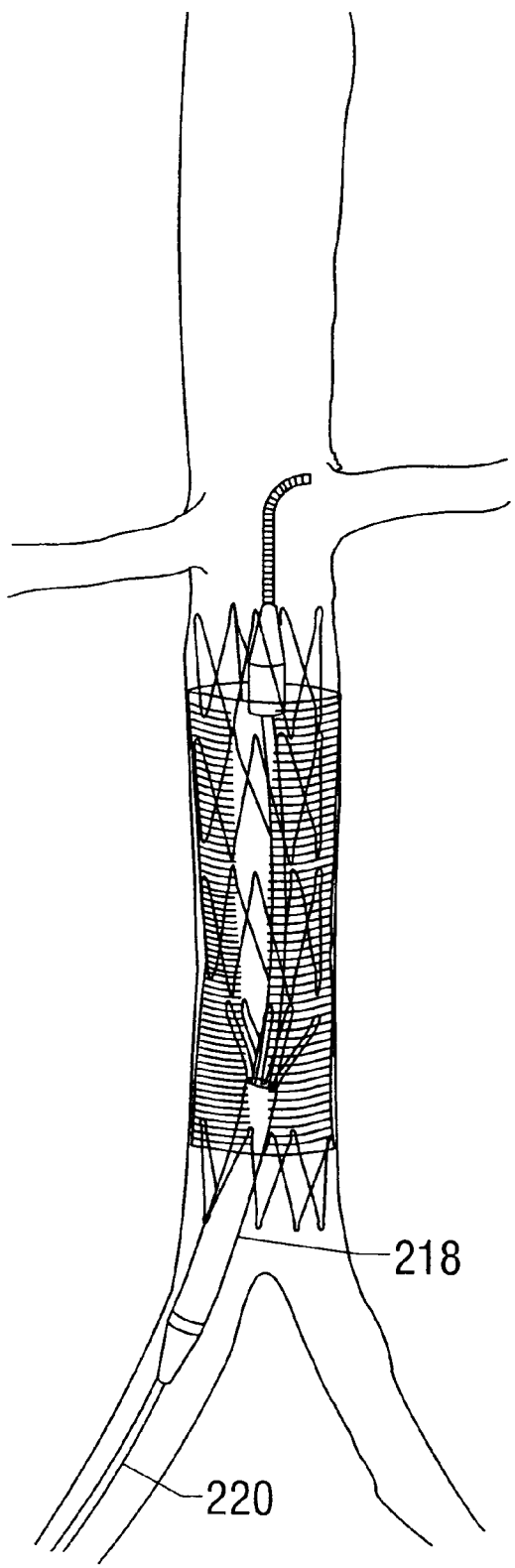
FIG. 23 is a perspective view depicting the release of stage 2 into stage 1 using a double coaxial delivery system according to one embodiment of the present invention.

In the second step of the delivery shown in FIG. 23, the 10-F OD sheath /4-F catheter unit was withdrawn until the inner scaffolding stent was positioned within the lumen of the polyester tube between the two anchoring stents. Once the inner scaffolding stent was in place, the pusher wire was held stationary and the stent was released from the 10-F OD Teflon sheath 218 by pulling the 4-F catheter 220 back.

Once the graft was deployed, the delivery system was completely removed from the animal. Aortography was then repeated.

RESULTS

Graft delivery was uneventful and completely successful in all cases. The insertion and advancement of the delivery system was easy and smooth. The parts of the delivery system and the graft were adequately radiopaque so every moment of graft delivery and deployment could be easily monitored under fluoroscopy.

Using the front anchoring stent of the covered portion of the graft for guidance of the first step of deployment, accurate placement of the first stage was achieved in all cases. The front anchoring stent was successfully positioned infrarenally, just below the orifice of the more caudal renal artery.

Graft deployment was prompt and continuous, and less than two minutes elapsed between placement of the two separate graft parts. Both coaxial delivery mechanisms worked dependably and smoothly. No dislodgment of the first stage or entanglement of the delivery system in the graft material occurred during positioning and deployment of the second stage of the graft.

It is to be understood that the present invention is by no means limited to the specific embodiments which have been illustrated and described herein and that various modifications thereof may indeed be made. All of the methods and apparatus disclosed and claimed herein can be made and executed without undue experimentation in light of the present disclosure. While the apparatus and methods of this invention have been described in terms of illustrative embodiments, it will be apparent to those of skill in the art that variations may be applied to the apparatus and in the steps or in the sequence of of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An apparatus for delivering a stent graft having first and second stages, comprising:
   a first sheath having a first portion configured to enclose the first stage, the first sheath also having a second portion smaller than the first portion; and
   a second sheath configured to enclose the second portion of the first sheath, the second sheath also being configured to enclose the second stage.

2. The apparatus of claim 1, further comprising:
   a pusher wire configured to fit within the first sheath, the pusher wire having an end.

3. The apparatus of claim 2, further comprising:
   a tip coupled to the end of the pusher wire, the tip being configured to facilitate manipulation of the apparatus within a vessel.

4. The apparatus of claim 2, further comprising:
   a first blocking piece coupled to the pusher wire in spaced relation with the end of the pusher wire; and
   a second blocking piece coupled to the pusher wire between the end of the pusher wire and the first blocking piece.

5. The apparatus of claim 1, further comprising:
   a catheter configured to enclose the second portion of the first sheath, the catheter also being configured to fit within the second sheath.

6. The apparatus of claim 1, wherein the first sheath comprises one contiguous piece.

7. The apparatus of claim 1, further comprising:
   one or more fluid openings defined in the second portion of the first sheath.

8. The apparatus of claim 1, further comprising:
   a blocking piece coupled to the second portion of the first sheath.

9. The apparatus of claim 1, further comprising:
   a microtubing configured to fit within the first sheath, the microtubing having an end.

10. The apparatus of claim 9, further comprising:
    a guiding mechanism in operative relation to the end of the microtubing, the guiding mechanism being configured to facilitate manipulation of the apparatus within a vessel.

11. The apparatus of claim 10, wherein the guiding mechanism comprises a guidewire configured to fit within the microtubing.

12. The apparatus of claim 10, wherein the guiding mechanism comprises a tip coupled to the end of the microtubing.

13. A stent graft delivery system, comprising:
    a pusher wire having an end;
    a tip coupled to the end of the pusher wire and configured to facilitate manipulation of the system within a vessel;
    a first blocking piece coupled to the pusher wire in spaced relation with the end of the pusher wire;
    a first sheath configured to enclose the pusher wire, the first sheath having a first portion configured to enclose the first blocking piece and an inner stage of a multi-stage stent graft, the first sheath also having a second portion smaller than the first portion; and
    a second sheath configured to enclose the second portion of the first sheath and an outer stage of the multi-stage stent graft.

14. The system of claim 13, further comprising:
    a catheter configured to enclose the second portion of the first sheath, the catheter also being configured to fit within the second sheath.

15. The system of claim 13, further comprising:
    a second blocking piece coupled to the second portion of the first sheath.

16. The system of claim 13, further comprising:
    a second blocking piece coupled to the pusher wire between the tip and the first blocking piece.

17. The system of claim 13, wherein the first sheath comprises one contiguous piece.

18. The system of claim 13, further comprising:

the inner stage configured to be compressed so as to fit within the first portion of the first sheath, the inner stage having a plurality of radially compressible spring stents connected by connecting bars;

the outer stage configured to be compressed so as to fit within the second sheath, the outer stage having two radially compressible spring stents connected by a connecting bar; and a graft material for enclosing the outer stage, the graft material being coupled to the outer stage such that a portion of one of the two radially compressible spring stents of the outer stage may contact a vessel upon delivery of the outer stage into the vessel.

19. The system of claim 18, wherein the inner and outer stages are each formed from a single wire.

20. The system of claim 18, wherein the graft material is polyester.

21. The system of claim 13, further comprising:

a self-expanding tube stent configured to be constrained so as to fit within the first portion of the first sheath.

22. The system of claim 13, further comprising:

a self-expanding tube stent configured to be constrained so as to fit within the second sheath.

23. The system of claim 13, further comprising:

one or more fluid openings defined in the second portion of the first sheath.

24. A delivery system for inserting and releasing a stent graft having first and second stages into a vessel, the system comprising:

a first sheath for releasing the first stage into the vessel; and a second means for releasing the second stage into the first stage, the second means positioned so as to be inserted into the vessel before the first sheath is inserted into the vessel.

25. The system of claim 24, wherein the second means comprises a second sheath.

26. The system of claim 24, wherein the second means comprises a second sheath having a first portion having a first caliber, the second sheath also having a second portion having a second caliber, the second caliber being smaller than the first caliber.

27. The system of claim 26, wherein the second sheath is formed from one contiguous piece.

28. The system of claim 26, further comprising:

one or more fluid openings defined in the second portion of the second sheath.

29. The system of claim 24, further comprising a catheter for holding the first stage in position during delivery thereof, the catheter being in operative relation with the first sheath.

30. The system of claim 24, wherein the first stage comprises two radially compressible spring stents connected by a connecting bar, and a graft material for enclosing the first stage, the graft material being coupled to the first stage such that a portion of one of the two radially compressible spring stents of the first stage may contact a vessel upon delivery of the first stage into the vessel.

31. The system of claim 24, wherein the second stage comprises a plurality of radially compressible spring stents connected by connecting bars.

32. The system of claim 24, wherein the first stage is a self-expanding tube stent.

33. The system of claim 24, wherein the second stage is a self-expanding tube stent.

34. A stent graft delivery system, comprising:

a pusher wire having an end;

a tip coupled to the end of the pusher wire and configured to facilitate manipulation of the system within a vessel;

a first blocking piece coupled to the pusher wire in spaced relation with the end of the pusher wire;

a second blocking piece coupled to the pusher wire between the end of the pusher wire and the first blocking piece;

a first sheath configured to enclose the pusher wire, the first sheath having a first portion configured to enclose the first blocking piece, the first portion having a first caliber, the first sheath also having a second portion having a second caliber smaller than the first caliber;

a second sheath configured to enclose the second portion of the first sheath; and a catheter configured to enclose to enclose the second portion of the first sheath, the catheter also being configured to fit within the second sheath.

35. A method of endovascularly assembling a stent graft in an aorta, comprising the steps of:

providing a self-expanding inner stage;

providing a self-expanding outer stage;

inserting the stages into the aorta in a single percutaneous insertion through a femoral artery;

positioning the stages within the aorta, the self-expanding inner stage being located cephalad of the self-expanding outer stage;

releasing the self-expanding outer stage;

positioning the self-expanding inner stage within the self-expanding outer stage;

releasing the self-expanding inner stage into the self-expanding outer stage so as to endovascularly assemble the stent graft.

36. A method for endovascularly assembling a stent graft having an inner stage enclosed by a leading sheath and an outer stage enclosed by a trailing sheath, the method comprising the steps of:

inserting the inner stage and the outer stage into a vessel, the stages being positioned such that the inner stage is inserted into the vessel before the outer stage is inserted into the vessel;

positioning the outer stage within the vessel;

pulling back the trailing sheath so as to release the outer stage;

withdrawing the inner stage so as to position it within the outer stage; and releasing the inner stage into the outer stage so as to endovascularly assemble the stent graft.

37. The method of claim 36, wherein the step of releasing the inner stage comprises pulling back the leading sheath so as to release the inner stage.

38. The method of claim 36, wherein the vessel is an aorta, an iliac artery, an inferior vena cava, or a superior vena cava.

39. The method of claim 36, wherein the vessel is an aorta or an iliac artery.

40. The method of claim 36, wherein the vessel is an aorta.

41. The method of claim 36, wherein the step of inserting comprises inserting the inner stage and the outer stage into an aorta in a single percutaneous insertion in a femoral artery.

42. A stent graft delivery system, comprising:

a microtubing having an end;

a guiding mechanism in operative relation to the end of the microtubing and being configured to facilitate manipulation of the system within a vessel;

a first blocking piece coupled to the microtubing in spaced relation with the end of the microtubing;

a first sheath configured to enclose the microtubing, the first sheath having a first portion configured to enclose the first blocking piece, the first portion having a first caliber, the first sheath also having a second portion having a second caliber smaller than the first caliber;

a second sheath configured to enclose the second portion of the first sheath; and a catheter configured to enclose the second portion of the first sheath, the catheter also being configured to fit within the second sheath.

43. The system of claim 42, wherein the guiding mechanism comprises a guidewire configured to fit within the microtubing.

44. The system of claim 42, wherein the guiding mechanism comprises a tip coupled to the end of the microtubing.

45. The system of claim 42, wherein the microtubing is made of nitinol.

46. The system of claim 42, wherein the first sheath comprises one contiguous piece.

47. The system of claim 42, further comprising:

an inner stage configured to be compressed so as to fit within the first portion of the first sheath, the inner stage having a plurality of radially compressible spring stents connected by connecting bars;

an outer stage configured to be compressed so as to fit within the second sheath, the outer stage having two radially compressible spring stents connected by a connecting bar; and a graft material for enclosing the outer stage, the graft material being coupled to the outer stage such that a portion of one of the two radially compressible spring stents of the outer stage may contact a vessel upon delivery of the outer stage into the vessel.

48. The system of claim 47, wherein the inner and outer stages are each formed from a single wire.

49. The system of claim 47, wherein the graft material is polyester.

50. The system of claim 42, further comprising:

a self-expanding tube stent configured to be constrained so as to fit within the first portion of the first sheath.

51. The system of claim 42, further comprising:

a self-expanding tube stent configured to be constrained so as to fit within the second sheath.

52. The system of claim 42, further comprising:

one or more fluid openings defined in the second portion of the first sheath.

53. The system of claim 42, further comprising:

a second blocking piece coupled to the microtubing between the first blocking piece and the end of the microtubing.

54. A stent graft delivery system, comprising:

a microtubing having an end;

a guiding mechanism in operative relation to the end of the microtubing and being configured to facilitate manipulation of the system within a vessel;

a first blocking piece coupled to the microtubing in spaced relation with the end of the microtubing;

a first sheath configured to enclose the microtubing, the first sheath having a first portion configured to enclose the first blocking piece, the first portion having a first caliber, the first sheath also having a second portion having a second caliber smaller than the first caliber;

a second sheath configured to enclose the second portion of the first sheath; and a second blocking piece coupled to the second portion of the first sheath.

55. The system of claim 54, wherein the guiding mechanism comprises a guidewire configured to fit within the microtubing.

56. The system of claim 54, wherein the guiding mechanism comprises a tip coupled to the end of the microtubing.

57. The system of claim 54, wherein the microtubing is made of nitinol.

58. The system of claim 54, wherein the first sheath comprises one contiguous piece.

59. The system of claim 54, further comprising:

one or more fluid openings defined in the second portion of the first sheath.

60. The system of claim 54, further comprising:

a third blocking piece coupled to the microtubing between the first blocking piece and the end of the microtubing.

61. The delivery system of claim 54, wherein the second blocking piece is coupled to the second portion of the first sheath in a location, the location being such that the second blocking piece is positioned within the second sheath during a phase of the operation of the system.

62. An apparatus for delivering a stent graft having first, second and third stages, comprising:

a first sheath having a first portion configured to enclose the first stage, the first sheath also having a second portion smaller than the first portion;

a second sheath configured to enclose the second portion of the first sheath, the second sheath also being configured to enclose the second stage, the second sheath also having a second portion smaller than the first portion of the second sheath; and a third sheath configured to enclose the second portion of the second sheath, the third sheath also being configured to enclose the third stage.

63. The apparatus of claim 62, further comprising:

a pusher wire configured to fit within the first sheath, the pusher wire having an end.

64. The apparatus of claim 63, further comprising:

a first blocking piece coupled to the pusher wire in spaced relation with the end of the pusher wire;

a second blocking piece coupled to the second portion of the first sheath; and a catheter configured to enclose the second portion of the second sheath, the catheter also being configured to fit within the third sheath.

65. The apparatus of claim 62, wherein the first sheath comprises one contiguous piece.

66. The apparatus of claim 62, wherein the second sheath comprises one contiguous piece.

67. The apparatus of claim 62, wherein the second portion of the second sheath includes one or more fluid openings defined therein.

68. The apparatus of claim 62, further comprising:

a microtubing configured to fit within the first sheath, the microtubing having an end.

69. The apparatus of claim 68, further comprising:

a guidewire configured to fit within the microtubing;

a first blocking piece coupled to the microtubing in spaced relation with the end of the microtubing;

a second blocking piece coupled to the second portion of the first sheath; and a catheter configured to enclose the second portion of the second sheath, the catheter also being configured to fit within the third sheath.

* * * * *

UNITED STATES PATENT AND TRADEMARK OFFICE
CERTIFICATE OF CORRECTION

PATENT NO. : 6,123,723
DATED : September 26, 2000
INVENTOR(S) : Konya et al.

It is certified that error appears in the above-identified patent and that said Letters Patent is hereby corrected as shown below:

Title page, item [54],
Line 2, please delete "DEPOLYMENT" and insert -- DEPLOYMENT -- therefor.

Claim 15, column 32,
Line 62, after "the first sheath", please insert -- in a location, the location being such that the second blocking piece is positioned within the second sheath during operation of the apparatus -- therefor.

Claim 34, column 34,
Line 15, please delete one instants of the phrase "to enclose".

Signed and Sealed this

Eighteenth Day of September, 2001

Attest:

*Nicholas P. Godici*

NICHOLAS P. GODICI
*Attesting Officer*    *Acting Director of the United States Patent and Trademark Office*